(12) United States Patent
Dasgupta et al.

(10) Patent No.: US 7,314,718 B1
(45) Date of Patent: Jan. 1, 2008

(54) METHOD AND APPARATUS FOR MAINTAINING MULTIPLE PLANAR FLUID FLOWS

(75) Inventors: Purnendu Kumar Dasgupta, Lubbock, TX (US); Kazimierz Surowiec, Lublin (PL); Jordan Mitchell Berg, Lubbock, TX (US)

(73) Assignee: BioArray Solutions Ltd., Warren, NJ (US)

( * ) Notice: Subject to any disclaimer, the term of this patent is extended or adjusted under 35 U.S.C. 154(b) by 658 days.

(21) Appl. No.: 10/115,417

(22) Filed: Apr. 3, 2002

Related U.S. Application Data

(60) Provisional application No. 60/310,361, filed on Aug. 6, 2001, provisional application No. 60/281,059, filed on Apr. 3, 2001.

(51) Int. Cl.
*G01N 33/53* (2006.01)
(52) U.S. Cl. .................................... 435/7.1
(58) Field of Classification Search ............ 435/4, 435/7.1, 5–7.5, 7.8, 7.91–7.95; 422/55–63, 422/68.1–73; 436/514–519, 523
See application file for complete search history.

(56) References Cited

U.S. PATENT DOCUMENTS

| | | | | |
|---|---|---|---|---|
| 4,920,056 | A | 4/1990 | Dasgupta et al. | 436/50 |
| 5,187,096 | A * | 2/1993 | Giaever et al. | 435/287.1 |
| 5,716,852 | A * | 2/1998 | Yager et al. | 436/172 |
| 6,068,818 | A | 5/2000 | Ackley et al. | 422/50 |
| 6,086,736 | A | 7/2000 | Dasgupta et al. | 204/453 |
| 6,106,685 | A * | 8/2000 | McBride et al. | 204/600 |
| 6,167,910 | B1 * | 1/2001 | Chow | 137/827 |
| 6,200,814 | B1 * | 3/2001 | Malmqvist et al. | 436/52 |
| 6,254,827 | B1 | 7/2001 | Ackley et al. | 422/68.1 |
| 6,264,825 | B1 * | 7/2001 | Blackburn et al. | 205/777.5 |
| 6,267,858 | B1 | 7/2001 | Parce et al. | 204/600 |
| 6,268,219 | B1 | 7/2001 | Mcbride et al. | 436/180 |
| 6,309,602 | B1 | 10/2001 | Ackley et al. | 422/68.1 |
| 6,319,472 | B1 | 11/2001 | Ackley et al. | 422/68.1 |
| 6,321,791 | B1 | 11/2001 | Chow | 137/833 |
| 6,540,895 | B1 * | 4/2003 | Spence et al. | 204/450 |
| 6,645,432 | B1 * | 11/2003 | Anderson et al. | 422/100 |
| 6,779,559 | B2 * | 8/2004 | Parce et al. | 137/806 |

FOREIGN PATENT DOCUMENTS

WO    WO 02/01184    1/2002

OTHER PUBLICATIONS http://www.erc.montana.edu/~paul_s/biofilm_flow.htm; Flow Cells and Image Analysis; May 22, 2002.

* cited by examiner

*Primary Examiner*—Ann Y Lam
(74) *Attorney, Agent, or Firm*—Eric P. Mirabel

(57) ABSTRACT

The present invention provides a method of performing analyses and assays involving multiple interactions of reagent-containing fluid flows with liquid and solid target substances. The methods of the invention allow the simultaneous manipulation of different fluids on a small planar surface. The invention also provides a flow cell and method of use thereof for analyzing fluid-fluid and fluid-solid interactions in a substantially planar system. The flow cell contains at least one chamber and a plurality of inlets thereto allowing the introduction of a plurality of fluids in fluidic contact. The cell depth is the smallest dimension of the flow cell, and is of a magnitude, from about 50 to about 1000 microns such that any mixing of adjacent fluids in the chamber is substantially limited to mixing by passive diffusion. Interactions between reagents in fluids and target substances maintained in the fluid cell, or interactions between diffusion-mixed reagents in adjacent fluids, may be analyzed by standard analysis methods.

29 Claims, 18 Drawing Sheets

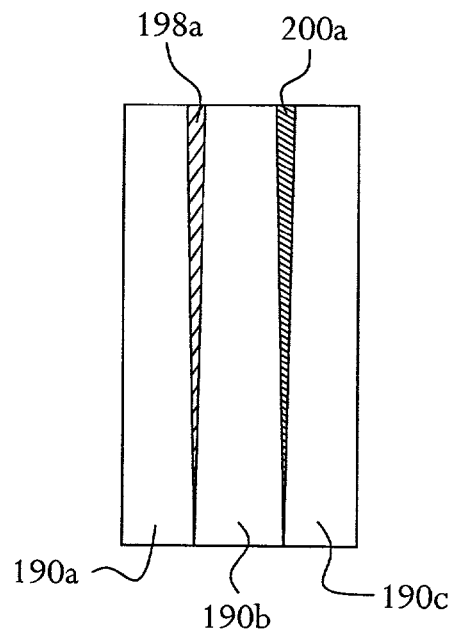
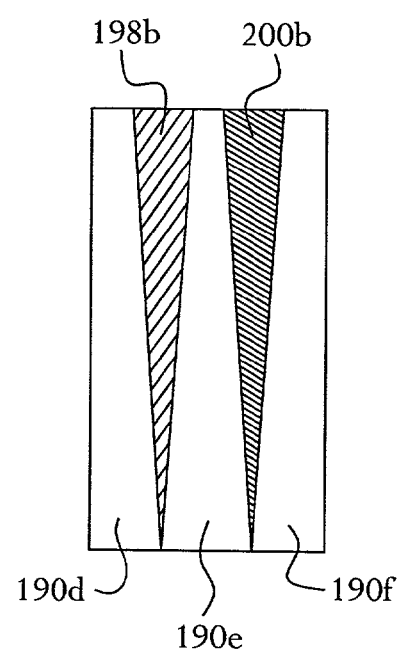
FIG. 13A  FIG. 13B
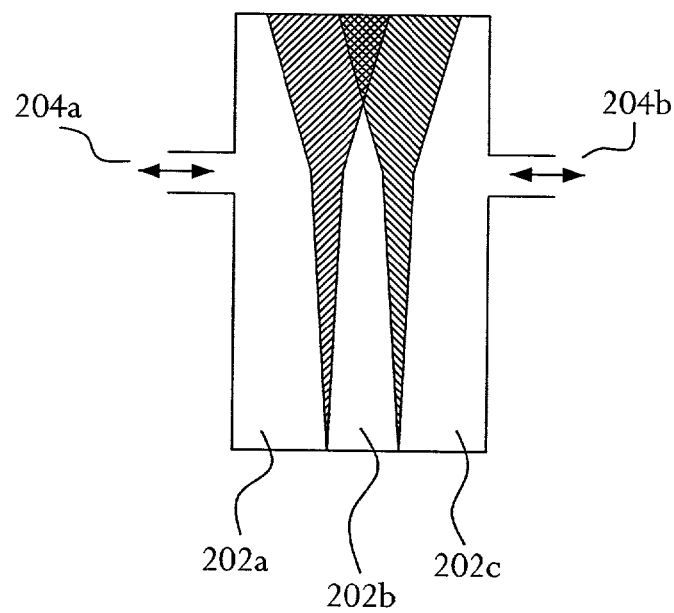
FIG. 13C

METHOD AND APPARATUS FOR MAINTAINING MULTIPLE PLANAR FLUID FLOWS

CROSS REFERENCE TO RELATED APPLICATION

This application claims the priority of now abandoned U.S. Provisional Applications Ser. Nos. 60/281,059 filed Apr. 3, 2001 and 60/310,361 filed Aug. 6, 2001, the entire disclosures of which are incorporated herein by reference.

FIELD OF THE INVENTION

The present invention relates to the methods and apparatus for conducting assays utilizing multiple fluid flows, either constant or intermittent flow, in parallel.

BACKGROUND OF THE INVENTION

A significant challenge in modern research in many fields is the need for miniaturization and increased speed in the performance of biological assays without any loss in the level of quality and accuracy.

Biological assays have been performed using colorimetric techniques requiring the addition of one or more reagents to form a measurable reaction product which is monitored.

In some assays, relying on a single sample analysis, more than one analyte must be measured simultaneously to provide a meaningful result. Examples of such assays involve the determination of glucose and cholesterol content in a blood plasma sample. In other assays, it is necessary to quantify the behavior of a cell population as it is exposed to a chemical stimulus. An example of such an assay involves monitoring the change in intracellular calcium levels upon repeated exposure to a drug substance. Such an assay employs a fluorescent calcium marker agent to indicate intracellular calcium levels.

Assay conditions for one analyte often differ from those of another, and may further employ reagents that are incompatible with each other. Thus, individual assays can rarely be conducted for multiple analytes simultaneously in the same reaction phase, but rather must be conducted in parallel in independent experiments.

Prior art techniques have aimed, by varied and often complex means, to parallize protocols in biological assays and to increase the speed at which such assays can be conducted. This quest for speed and parallelization has generally involved the need to miniaturize the instruments used with such assays to account for a lower reagent requirements and shorter transport paths.

In some assays, different analytes in a sample can only be determined after some separation is performed. Liquid chromatographic and in recent years electrophoretic separations in tubes or microfabricated channels have been used as separation techniques.

Microfluidic devices have been fabricated in recent years to address many of the issues raised by the increased throughput demands of biological assays. The development of these devices has been the beneficiary of advancements in microfabrication technology originally applied in the electronics and semiconductor industries. Technologies that include photolithography, wet chemical etching and even injection molding of polymers have been applied in the fabrication of microscale channels and wells that form the conduit networks of microfluidic flow cells used in many assays. However, though microfluidic devices have increased throughput by decreasing sample and reagent requirements and reducing flow path and component size, they remain largely devices that perform the analysis of one sample at a time and are not amenable to simultaneous multi-sample analysis.

In order to allow for conducting simultaneous multi-sample analyses in a single assay format, it would therefore be desirable to provide methods and apparatus that are not limited to single sequential analyses. The present invention meets these and other needs.

SUMMARY OF THE INVENTION

In one embodiment, the present invention provides a method for analyzing an interaction between a reagent and a target substance. The method comprises three steps. The first step is providing two or more fluid flows in a common plane. They may be either continuous or intermittent. But though adjacent flows are in fluidic contact, they do not intermix except by passive diffusion. At least one of the fluid flows comprises a reagent. The second step is contacting one or more of the reagent-containing flows with one or more target substances. The third step is analyzing an interaction between a reagent and a target substance.

In another embodiment, there is provided a method for performing an assay. This method comprises first introducing into a reaction vessel two or more fluids. In this method, adjacent fluids are in fluidic contact but do not intermix except by passive diffusion. At least one of the fluids contains a first analyte. The second step is contacting the first analyte with a second analyte, the second analyte being contained within the reaction vessel. The last step is analyzing a product of an interaction of the first analyte with the second analyte More than one of the two or more fluids may contain a first analyte. Thus, more than one first analyte, either the same or different may be introduced into the reaction vessel and may contact one, or more than one second analyte which may be the same or different.

In another embodiment of the present invention there is provided a flow cell comprising a top wall and a bottom wall in parallel spaced relation defining a chamber therebetween. Inlets are provided for introducing at least two fluids into the chamber in mutual fluidic contact. The spacing between the top and bottom walls is selected such that any mixing of the at least two fluids flowing in adjacent flows through the cell is substantially limited to mixing by passive diffusion.

In a sub-embodiment thereof, there is provided a flow cell, comprising n−1 substantially planar chambers, n walls, n−1 spacers, and at least n+1 ports, wherein n is an integer greater than one. In a sub-embodiment, there is provided the flow cell as described above, comprising one chamber.

In preferred embodiments, each chamber has dimensions comprising a length, a width and a depth, the chamber being bounded by top and bottom walls being held apart and substantially parallel by the spacer. The top wall has a flat inner surface facing the bottom wall, and inner surface has a perimeter area. The bottom wall has a flat inner surface facing the top wall, and the inner surface has a perimeter area. The spacer is positioned between the top wall and the bottom wall and defines the depth of the chamber. The spacer has a uniform thickness, and the spacer connects the perimeter of the inner surface of the top wall to the perimeter of the inner surface of the bottom wall, circumferencially enclosing the chamber.

Ports in a wall or a spacer between two of the walls at any location on the flow cell serve as inlets or outlets, and allow entry of fluids into at least one chamber. The space between the top and bottom walls and therefore the depth of the chamber of the flow cell is defined by the thickness of the spacer. The distance between the top and bottom walls is the smallest dimension of the flow cell, and is such that mixing of fluids in adjacent flows in the flow cell is substantially limited to mixing by passive diffusion.

In another embodiment, there is provided an apparatus for analyzing an interaction between a reagent and a target substance. The apparatus comprises a flow cell as described above operatively connected to at least one detector.

In a further embodiment of the invention, there is provided a method for analyzing an interaction between a reagent and a target substance. This method comprises the following steps. First an apparatus as described above is provided, which contains a flow cell and at least one detector. Second, two or more fluid flows are provided. These fluid flows are in a common plane and adjacent fluid flows are in fluidic contact but do not intermix except by passive diffusion. At least one of the fluid flows contains a reagent. Third, one or more of the reagent-containing flows makes contact with one or more of the target substances. Last, an interaction between a reagent and a target substance is analyzed.

These and other aspects of the invention are described in the detailed description and claimed in the claims that follow.

The term "analyte" means a substance being measured in an analytical procedure.

The term "beads" as used herein means colloidal particles which may be charged or nominally neutral, having a diameter in the range of about 0.02 microns to about 20 microns. Beads may be derivatized with chemical functional groups including peptides and may have cells, alive or dead adhered to the bead surface for solid phase handling.

The term "biota" as used herein means cells, dead or living, isolated cell fractions and antibodies capable of binding biological molecules, such as for example, proteins, complex carbohydrates, glycoproteins, nucleic acids and phospholipids.

The term "fluidic contact" as used herein means intimate, direct, actual contact of one fluid with another fluid, which may be the same or a different.

The term "wall" as used herein in connection with a structural element of a flow cell, refers to a solid planar structural body.

The term "microfabricated" as used herein with respect to a structural element or feature of a device means that the element has at least one fabricated dimension in the range of from about 1 micron to about 1000 microns. Thus a device referred to as being microfabricated will include at least one structural feature having a dimension in that range. When used in regard to a fluidic element, such as a chamber or a conduit or a port, the terms "microfluidic" or "microscale" refer generally to one or more fluid ports, chambers or conduits which have at least one internal cross-sectional dimension, e.g., depth, width, diameter, etc., that is less than 1000 microns, and generally in the range of from about 1 micron to about 500 microns. In the devices and apparatus of the present invention, the flow cell comprises a substantially planar chamber wherein the depth in the range of 50-1000 microns, preferably in the range of 50-250 microns. Accordingly, the microfluidic devices and apparatus prepared in accordance with the present invention will include at least one microscale chamber.

The term "spacer" as used herein with respect to the flow cell of the invention, refers to an element which serves to separate a top wall from a bottom wall to provide the depth dimension for the chamber of the flow cell.

The term "port" refers to openings in the flow cell of the present invention, either through one of the walls or through the separation, often a spacer separating the walls. Such ports provide fluidic access to the chamber of the flow cell and comprise an inert tubing, such as polytetrafluoroethylene tubing. Prefabricated fittings for use with polytetrafluoroethylene tubing are well known in the art.

BRIEF DESCRIPTION OF THE DRAWINGS

FIG. 13A schematically depicts fluid band spreading in a flow cell of the invention and chemical reaction of reagents within the intermix zones of adjacent flows.

FIG. 13B schematically depicts the interaction of adjacent flows depicted in FIG. 13A, but at a lower flow rate which allows for substantially more fluid intermixing.

FIG. 13C schematically depicts enhanced intermixing of adjacent fluid flows achieved by driving forces oriented perpendicular to the main fluid flows.

DETAILED DESCRIPTION OF THE INVENTION

Figure 1:
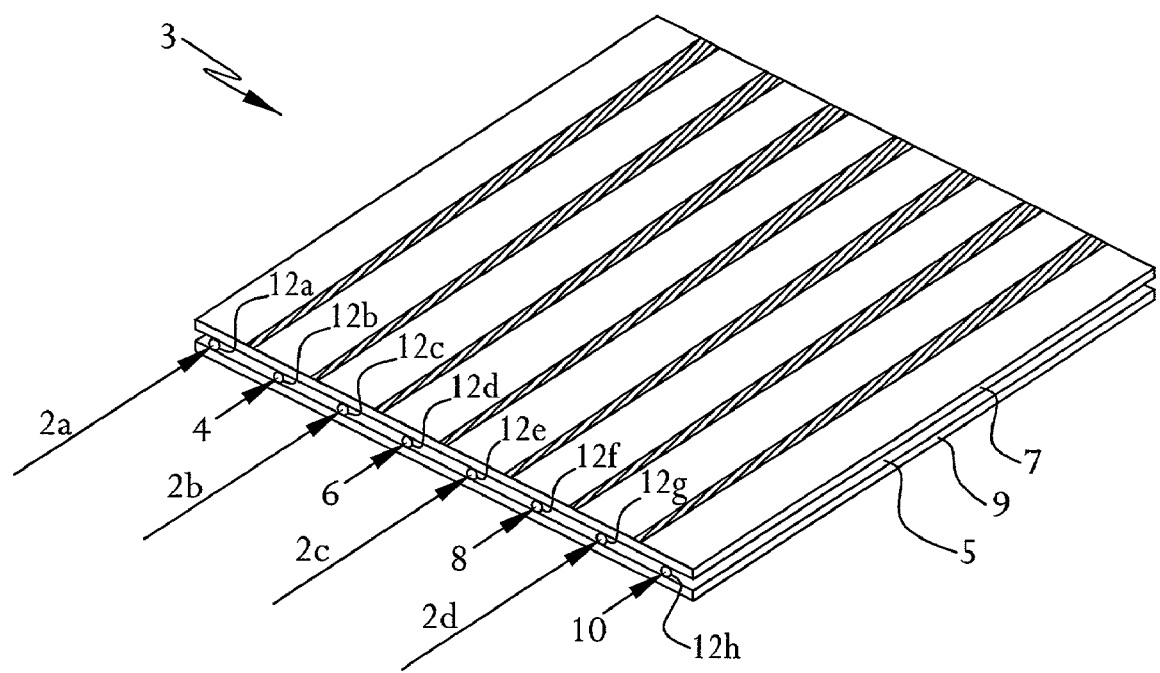
FIG. 1 is a schematic representation of fluid flow in a flow cell of the present invention.

The present invention provides for the simultaneous manipulation of different fluids on a small planar surface and for the analysis of multiple interactions of reagent-containing fluid flows with liquid target substances, and with solid target substances. Solid target substances of interest may comprise biological materials such as biota, i.e., live or dead cells, isolated cell fractions and antibodies capable of binding biological molecules. Solid target substances may further comprise beads derivatized with chemical functional groups, biological molecules or cells.

The terms "reagent" and "target substance" are functional terms used to differentiate components of an interaction which is to be analyzed. Typically a reagent is a substance of known properties and reactivity and a target substance is considered the entity to be characterized in a particular assay or analysis. It may be appreciated that in some circumstances a target substance in one reaction may serve as a reagent in a subsequent interaction. For example, a target substance may be derivatized by reaction with a reagent. Subsequently interactions may be monitored between the derivatized target substance and additional target substances in a reaction such as a homocoupling.

According to the present invention, adjacent fluid flows are in fluidic contact but do not substantially intermix even though no physical boundaries are present between them. We have found that intermixing beyond slow passive diffusion does not occur in adjacent fluids in fluidic contact if the fluid depth is maintained in the range of from about 50 to about 1000 microns. Preferably, the fluid depth is maintained in the range of from about 50 to about 250 microns, more preferably from about 50 to about 100 microns. When the fluid depth is maintained in this range, intermixing of adjacent flows is very slow, limited essentially to passive diffusion. Fluid particle travel over a distance of only a few millimeters may take several hours by passive diffusion, thus sharp boundaries are maintained between different fluids at short flow cell residence times.

A flow cell generally is a device that is a component of a conduit through which a fluid flows in constant or intermittent flow, for sampling of small volumes of fluid for analyses without the necessity for removal of aliquots for separate analysis. A flow cell is configured to contain a flowing sample for analyses in the same way that a cuvette would hold a static sample for an analyses such as UV, visible or infrared absorbance. Also like a cuvette, the composition and size of a flow cell are determined by the type of analysis desired, i.e., UV absorption would require a material to efficiently transmit ultraviolet light at the wavelength of interest, and would require a consistent path length for the light path through the cell.

According to the present invention, novel flow cells are constructed to provide for multiple discrete fluid flows, and methods of analyses are provided which utilize such cells. Flow cells of the invention can thus maintain adjacent substantially discrete fluid flows which are in intimate, fluidic contact but can be interacted separately with one or more target substances maintained in the flow path. Interactions between the fluids and target substances in the flow paths may be separately and independently analyzed.

According to another aspect of the invention, the slow but finite intermixing of adjacent fluid flows by passive diffusion may be harnessed for analytical purposes. The degree of intermixing by passive diffusion may be controlled by adjusting the flow rates, by adjusting the length of the flow path or by modifying the depth of the flow cell. Fluid coverage of the flow cell is governed by fluid inlet and outlet geometries, relative fluid velocities, and fluid viscosities, such that flow cell architecture and experimental design can widely vary the flow geography in the flow cell.

This controlled interaction of materials in adjacent fluid flows provides yet another format for bringing into controlled contact two or more substances for interaction, and interaction analysis. Thus, one may rely on the separateness of adjacent fluid flows to interact those fluids separately with a target substance in the respective flow paths, and conduct analyses of such interactions in parallel. One may also rely on the controlled mixing of adjacent fluid flows by passive diffusion to provide a ternary interaction between an intermixed pair of adjacent fluid flows and a target substance in the path of the intermix flow portion.

In the simplest embodiment, a single chamber flow cell of the invention contains top and bottom walls maintained in spaced relationship. Where multi-chamber cells are maintained in stacked relation (e.g., FIG. 15), the top wall of one cell also serves as the bottom wall of the cell immediately overhead. Thus, with respect to cell construction, "top" and "upper" on the one hand, and "bottom" or "lower" on the other hand may be used interchangeably in discussing the orientation of the walls forming the flow cells of the invention.

A variety of materials may be employed to form the walls of the flow cells of the invention. Generally, wall materials are selected from those compatible with common microfabrication techniques such as photolithography, wet chemical etching, laser ablation, air abrasion techniques, injection molding, embossing and other techniques. Wall materials may be selected based on compatibility with the conditions to which such a device may be exposed during use, e.g., exposure to organic solvents, wide variations in pH, temperature, reactive solutes, application of electric fields and wide spectrum light sources. Wall materials may also be selected for electrokinetic properties such as surface potential, for their optical properties such as transparency to electromagnetic radiation, particularly in the visible and ultraviolet wavelength ranges or other properties related to the desired application. Accordingly, in some preferred aspects, the wall material may include materials generally associated with semiconductor technology where such microfabrication techniques have long been employed, including silica based materials such as glass, quartz, silicon, polysilicon, or fused silica.

In some embodiments of the flow cell of the invention, the top and/or bottom walls are composed of a material which transmits electromagnetic radiation of wavelengths in a range including at least visible and ultraviolet light. Such materials may comprise polymeric materials, e.g., plastics, such as, for example, polymethylmethacrylate (PMMA), polycarbonate, polytetrafluoroethylene (PTFE), polyvinyl chloride (PVC, and polydimethylsiloxane (PDMS). Such polymeric walls are readily manufactured using available microfabrication techniques, as described above, or from microfabricated masters, using well known molding techniques, such as injection molding, embossing, stamping, or by polymerizing the polymer precursor material within a selected mold. Such polymeric materials are preferred for their ease of manufacture, low cost/disposability and for their general inertness to many extreme reaction conditions. Any of the materials described above may optionally include treated surfaces, e.g., derivatized or coated surfaces to enhance their utility in the flow cell, e.g., to provide enhanced fluid direction, to modify electrokinetic properties, to provide selective sample retention properties or to provide additional stability to solvents or to other conditions of use.

In one embodiment, the top and/or bottom walls of the flow cell may be constructed of glass plates and the spacer comprises an about 50 micron gasket. The flow cell further comprises a recessed Plexiglas™ platform on which the bottom wall rests, and a top Plexiglas™ lid attached to the Plexiglas™ platform which provides a sealed case for the flow cell. A plurality of ports, which provide fluidic access to the chamber, are matched to a plurality of ports machined into the Plexiglas™ platform to allow fluid conduits to pass through the Plexiglas™ case and into the flow cell ports.

In certain embodiments of the invention, the fluid sandwiched between optically transparent top and bottom walls of a flow cell of the invention contains sufficient dissolved solutes such that the fluid has a refractive index greater than the refractive index of the top and bottom walls. The cell thus behaves as a planar liquid core waveguide (LCW). Light is efficiently transmitted in the liquid wall, permitting high sensitivity absorbance detection.

Two or more walls of the flow cell of the present invention are mated or connected together in spaced relation to form the microfluidic chamber or chambers of the flow cell. Connection of top and bottom walls may be carried out under any of a number of methods or conditions well known in the art including, for example, thermal bonding, or by employing adhesives. The top and bottom walls are maintained in spaced relationship by a spacer.

The spacer may take the form of a gasket between two substantially planar walls, e.g., a gasket comprising a polymer film. The gasket may be fitted into machined grooves in one or both walls which it connects. Alternately, a spacer may be incorporated into the structure of either the top or bottom wall. In another aspect, the spacer and the top and bottom walls may all be integrated in a one-piece structure such as, for example, in an injection-molded flow cell. The spacer generally connects the perimeter areas of the top and bottom walls to form a single contiguous chamber. In additional embodiments of the invention, the spacer is die cut to partition the chamber into multiple parallel channels that do not communicate fluidically with one another.

According to another embodiment, the bottom wall is made of silicon oxide coated silicon, and the top wall is made of glass, such as a square glass microscope slide cover slip; and the spacer is an about 50 micrometer thick KAPTON™ tape, said thickness including an adhesive.

The material forming the spacer may be selected based upon functional requirements of the spacer. Typically, materials are selected to provide a good seal for the flow cell. In addition, the spacer may be perforated to provide ports for the inflow and outflow of fluids.

The light transmission properties of the spacer may be selected to allow entry of light into the cell or to allow optical detection by a spectrophotometer communicating to the cell. Light transmission may be through the spacer itself or through an optical fiber penetrating the spacer. In some embodiments, the spacer is made of a material which transmits electromagnetic radiation of at least wavelengths in a range including visible and ultraviolet light.

Electromagnetic radiation may transmitted through the top and bottom walls of the flow cell and the contents thereof to a detector in a direct line. Alternatively, signals from the flow cell of the invention may be analyzed by fluorescence detection achieved by providing an electromagnetic radiation source through the top wall of the cell. The bottom wall of the flow cell is provided with a reflective coating or otherwise made of a reflective material. An appropriate detector positioned on the axis of fluid flow allows reading of a fluorescence signal that propagates along the fluid flow path. The fluorescence signal may optionally be transmitted to a remote detector by an optical fiber in communication with the chamber of the flow cell as described above. Alternatively the geometry required for fluorescence detection may be achieved by introducing electromagnetic radiation through he side of the flow cell, such as through the spacer via optical fibers as described above. The resulting fluorescence may be imaged through the top or bottom walls of the cell which transmit light in the desired wavelength. This technique is particularly valuable in imaging the entire flow cell simultaneously. The entire spacer composition may be selected to be of a high RI material compared to the to and bottom walls and thus act as a waveguide to bring light efficiently into the chamber. For short distances, such as those of less than 1 millimeter employed in a flow cell of the present invention, it is not essential that the spacer is a perfect light guide.

Figure 16A:
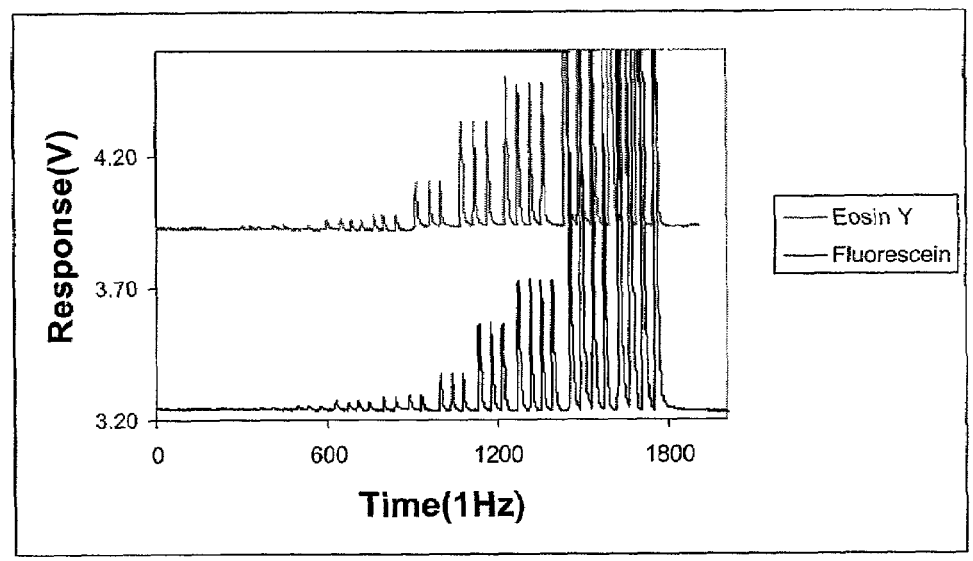
FIG. 16A shows graphical representations of fluorescence signal data for fluorescein and Eosin Y flowed through a flow cell and monitored by a fluorescence detector configured to detect through the top or bottom wall.
Figure 16B:
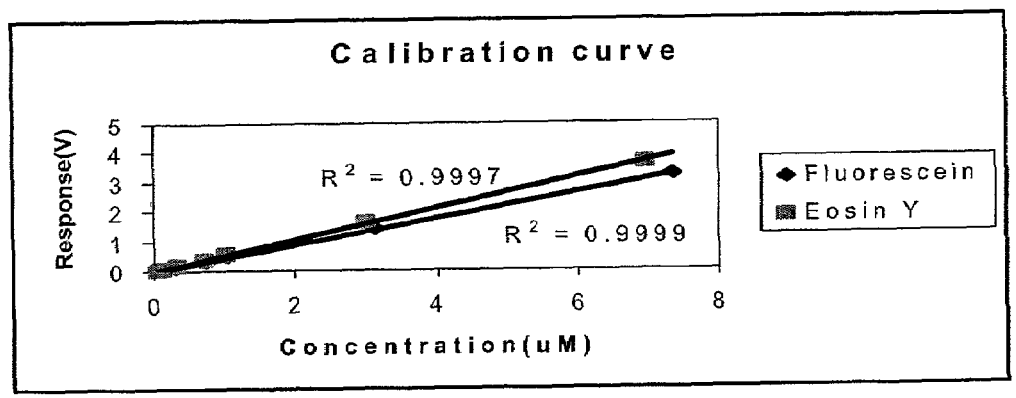
FIG. 16B shows the standard curves generated for a series of concentrations of fluorescein and Eosin Y using the data depicted in FIG. 16A.

In one embodiment of the present invention, a flow cell is provided, wherein a laser printer transparency (150 micron thick) was used as a spacer. The chamber, 3 mm wide, was illuminated by high brightness blue and green LED's. Dilute NaOH was flowed through the device and a miniature photomultiplier tube (Hamamatsu H5784) was placed directly on the optically transparent top wall with an intervening piece of red or yellow plastic acting as an excitation light filter. Dilute fluorescein and Eosin Y solutions were injected into the fluid flow and independent analyses of the two separate flows was performed simultaneously using fluorescence spectroscopy. The graphical fluorescence data for both substances is shown in FIG. 16A and the standard curves generated for fluorescein and Eosin Y concentrations are shown in FIG. 16B. Numerical data for these experiments is listed below in Table 1.

TABLE 1

Data for fluorescence response of fluorescein and Eosin Y.

| Concentration (µM) | Response, volts | |
| --- | --- | --- |
| | Fluorescein | Eosin Y |
| 0.03 | 0.016 | 0.016 |
| 0.07 | 0.033 | 0.039 |
| 0.1 | 0.052 | 0.058 |
| 0.3 | 0.142 | 0.168 |
| 0.7 | 0.333 | 0.395 |
| 1.0 | 0.496 | 0.531 |
| 3.0 | 1.391 | 1.634 |
| 7.0 | 3.216 | 3.667 |

The flow cells of the invention may be used to assay the interaction between reagents and target substances. Accordingly, two or more fluid flows are provided in a plane in the cell. The fluid flows can be continuous or they can be intermittent to permit sampling or analysis, such as by spectrophotometry. Interruption of the fluid flows has little effect on the degree of intermixing of adjacent fluid flows.

Intermixing remains limited to passive diffusion whether the fluid is flowing or static. At least one of the fluid flows comprises a reagent for interaction with a target substance. The target substance may comprise a liquid or a solid.

Contact between the reagent and target substance can be carried out in a variety of ways. In one embodiment, the target substance is maintained in the path of a fluid flow containing a reagent. In another embodiment, the target substance is dissolved or suspended in a first fluid flow which is adjacent to and in fluidic contact with a second fluid flow containing a reagent. The degree of passive diffusion intermixing permitted between the adjacent flows, and hence the degree of contact between reagent and target substance, may be controlled by adjusting the fluid flow depth and rate of flow. Thus, the degree of interaction may be controlled by controlling these parameters.

In another embodiment, the reagent is contained in a first fluid flowing in a plane, and the target substance is contained in a second fluid flowing in a plane orthogonal to the plane of the first fluid flow.

Where the target substance is solid, it may be positioned so that it is contacted by one or more fluid flows. In such embodiments of the invention, the target substance may comprise for example, beads, dead cells, live cells, cell fractions, beads with adherent live cells or dead cells, beads with adherent or chemically bonded biological chemicals, e.g., peptides, polypeptides, antigens, antibodies, oligonucleotides, polynucleotides, carbohydrates, polysaccharides, and the like, and beads with adherent or chemically bonded chemical functional groups.

It is possible to initiate a fluid flow without a reagent, and add the reagent to the fluid at a selected downstream location in the cell. In other embodiments a fluid flow may be established which does not contain a reagent and thus performs as a blank or a control when analyses are performed in parallel with other flows containing a reagent.

Generally, a flow of a fluid-containing reagent is initiated in the flow cell chamber by introducing the reagent flow through a port communicating with the cell chamber. In one embodiment of the present invention, the target substance is a cell culture and the reagent is a test compound, for example a test drug. Initially, the fluid flow may contain only a standard nutrient solution and no reagent. This nutrient solution may be flowed into contact with a plurality of cell cultures which may contain the same or different type cells. At a selected time in the procedure, a reagents are added to each fluid flow, wherein the reagents may be the same or different. Analysis of the cells may thus be performed while in contact with only the nutrient solution, and after contact with a reagent. Multiple different cell culture samples may be analyzed for interaction with the same reagent in this manner. Alternately, multiple samples of the same cell culture may be positioned at different locations such that different fluid flows (containing different reagents) contact different samples of the same cell culture. In the latter arrangement, the interaction of multiple reagents on the same target cell culture is analyzed. In the former arrangement, the interaction between a single reagent and multiple different target cell cultures is analyzed.

According to one embodiment of the latter arrangement, the same cell culture is contacted with combined first and second reagent-containing fluid adjacent fluid flows, containing different reagents. The flow rates of the individual fluid flows are adjusted to enlarge the region of passive diffusion intermixing therebetween as desired. Flow rates can be set in the range of from about 0.05 mL/min to about 0.25 mL/min, preferably from about 0.005 ml/min to about 0.01 mL/min, to provide significant intermixing. The result is a fluid flow profile comprising three zones: a flow zone containing only the first reagent, a flow zone containing only the second reagent, and an intermixed flow zone containing both the first and second reagent. The cell culture is placed in the path of the flow so as to be contacted with the intermixed flow and the separate flows. Thus, the analysis is of an interaction of different regions of the same target culture with the first reagent alone, the second reagent alone, and the intermix flow containing both reagents. If the example, the target substance were a cancer cell culture, and reagent-A and reagent-B were test drugs, analysis could be carried out in this fashion on the reagent-A/cell interaction, the reagent-B/cell interaction, and the combined reagent-A+reagent-B/cell interaction at the same time. This allows for convenient testing of multiple drug interactions on the same target cell types, including but not limited to testing for drug synergism. The possible synergistic effects of nutrients can be tested in the same manner. Because a flow cell of the present invention permits the simultaneous observation of several different fluid streams, the effects of multiple pairs of drugs/nutrients on the same or different cell populations can be studied simultaneously in a single flow cell chamber.

In another embodiment of the invention, the target substance may be a culture of motile cells. Using the tri-part flow profile described above, analysis of cell movements in and out of the various flow zones may be carried out.

Apparatuses in the form of flow cells, and analysis systems comprising such flow cells for carrying out the methods of the present invention, are illustrated in the appended drawings.

FIG. 1 shows a flow cell according to the present invention generally designated as 3. A planar chamber is formed between spaced apart parallel walls 5 and 7. The walls are maintained in spaced relation by a spacer 9 at the edge of the plates. Fluid flows 2a, 2b, 2c and 2d containing the identical target substance are introduced into the flow cell through respective ports 12a, 12c, 12e, and 12g in spacer 9. Fluid flows 4, 6, 8 and 10, each containing a different reagent, are introduced through respective ports 12b, 12d, 12f, and 12h. As the target substance/reagent flows elute through the flow cell, adjacent steams slowly intermix by passive diffusion. The zones of interaction between adjacent flows are indicated in FIG. 1 by cross-hatching. The interactions taking place in the interaction zone can be monitored or analyzed at any desired point in the axial flow of fluids along the flow cell. Alternatively, the interactions may be analyzed as the fluids exit the cell. Analysis within the cell can be during continuous flow or alternatively can be done under static conditions, i.e., with the flow stopped.

The embodiment of FIG. 1 has been described as utilizing multiple different reagents and a single target substance. It may be appreciated that the reverse arrangement may be employed utilizing the same flow cell construction, i.e., a single reagent interacted with multiple different target substances. Though the target substance is generally the entity to be tested and the reagent is generally a standard reagent used in a particular assay, the distinction between target substance and reagent is not absolutely necessary to the method of the present invention. Thus an entity which is a reagent may interact with a target substance to form a product which is itself a more synthetically advanced reagent or new target substance which has been derivatized or activated in preparation for interaction with yet another reagent.

Figure 2:
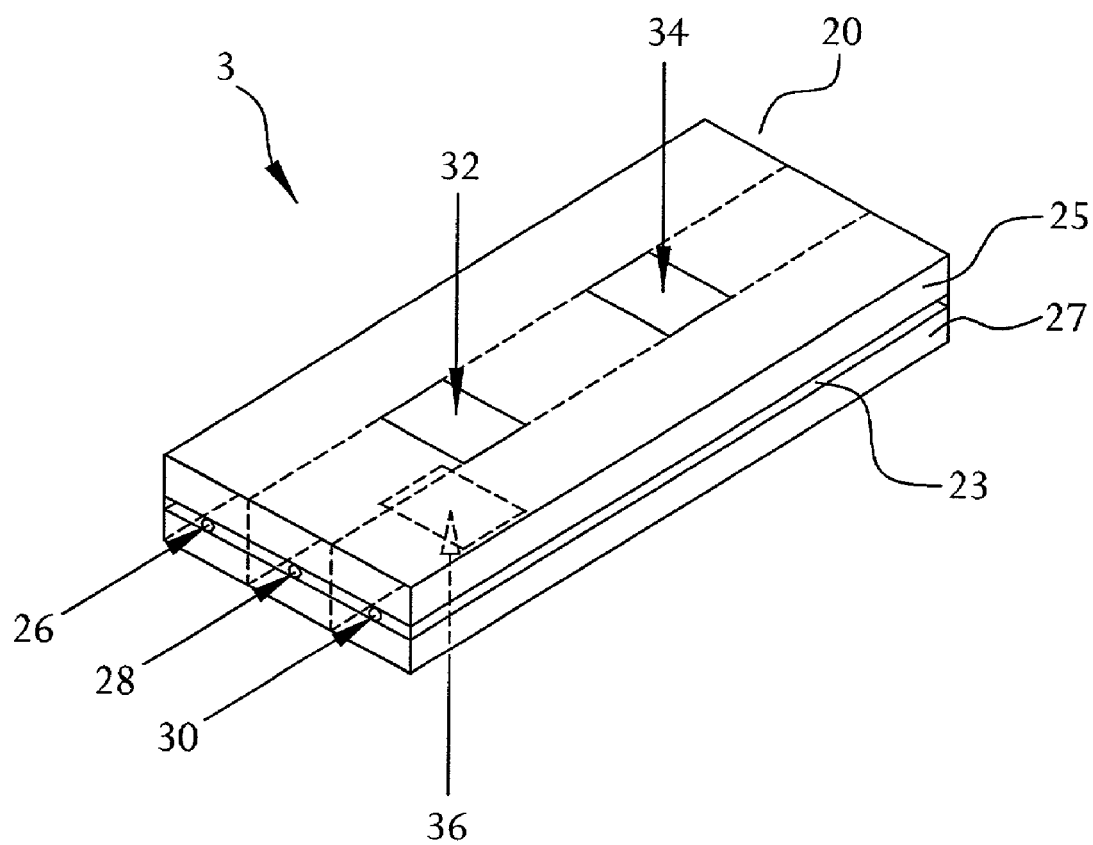
FIG. 2 shows a flow cell of the invention containing ports for adding reagents to the fluid flow.

FIG. 2 illustrates an embodiment of a flow cell of the present invention adapted to provide planar flows of fluid and also to receive reagent flowing in a direction orthogonal to the cell plane. The cell generally designated as 20 in FIG. 2 consists of spaced plates defining a flow chamber. Flows of reagents 26 and 30 and target substance 28 are introduced into the flow cell through respective inlets formed in spacer 23 at one end of the cell. Reagents 26 and 30 slowly intermix with substance 28 from both sides by passive diffusion. Additional reagents 32 and 36 are introduced into contact with the target substance through inlets (not shown) in the top and/or bottom plates establishing fluid flows orthogonal to and out of the plane of the flows of the target substance 28 and reagents 26 and 30. Reagents which are expensive, custom synthesized or otherwise in limited supply, wherein immediate and efficient mixing is desired, may be introduced in this manner as orthogonal fluid flows, either in constant flow or in pulses, through the top or bottom cell plates, or both. Because of the small vertical dimension, mixing is rapid for reagents introduced in this fashion. The orthogonal fluid flows may be established at the same or at different positions relative to the flow axis of the co-planar fluid flows.

Reagents 32 and/or 36 are permitted to react with the target substance and/or the products formed by interaction of the target substance with reagents 26 and 30. Thereafter, another reagent 34 is introduced in a similar manner. Thus, a synthetically advanced target substance could be formed by the sequential reaction of the original target substance with reagents 26 and 30 followed by reaction with reagents 32 and/or 36. This synthetically advanced target substance is then subjected to a latency period before contacting reagent 34.

It may be appreciated that reagents 32, 34 and 36 are introduced by orthogonal flow into the smallest dimension of the flow cell chamber. Hence mixing of these reagents with the fluid flow is fast and efficient. Reagents added by orthogonal flow can be added simultaneously for a single ternary reaction or sequentially to effect multiple separate reactions with the target substance (or the products formed by interaction of the target substance with in-plane flowing reagents such as 26 and 30). The latter technique yields the capacity of multiple high throughput reactions of advanced assay intermediates with multiple reagents. A complex assay may thus be performed in a single microfluidic device employing a flow cell of the present invention. This complex assay may optionally be done in parallel with multiple such assays performed on a single flow cell.

Figure 3:
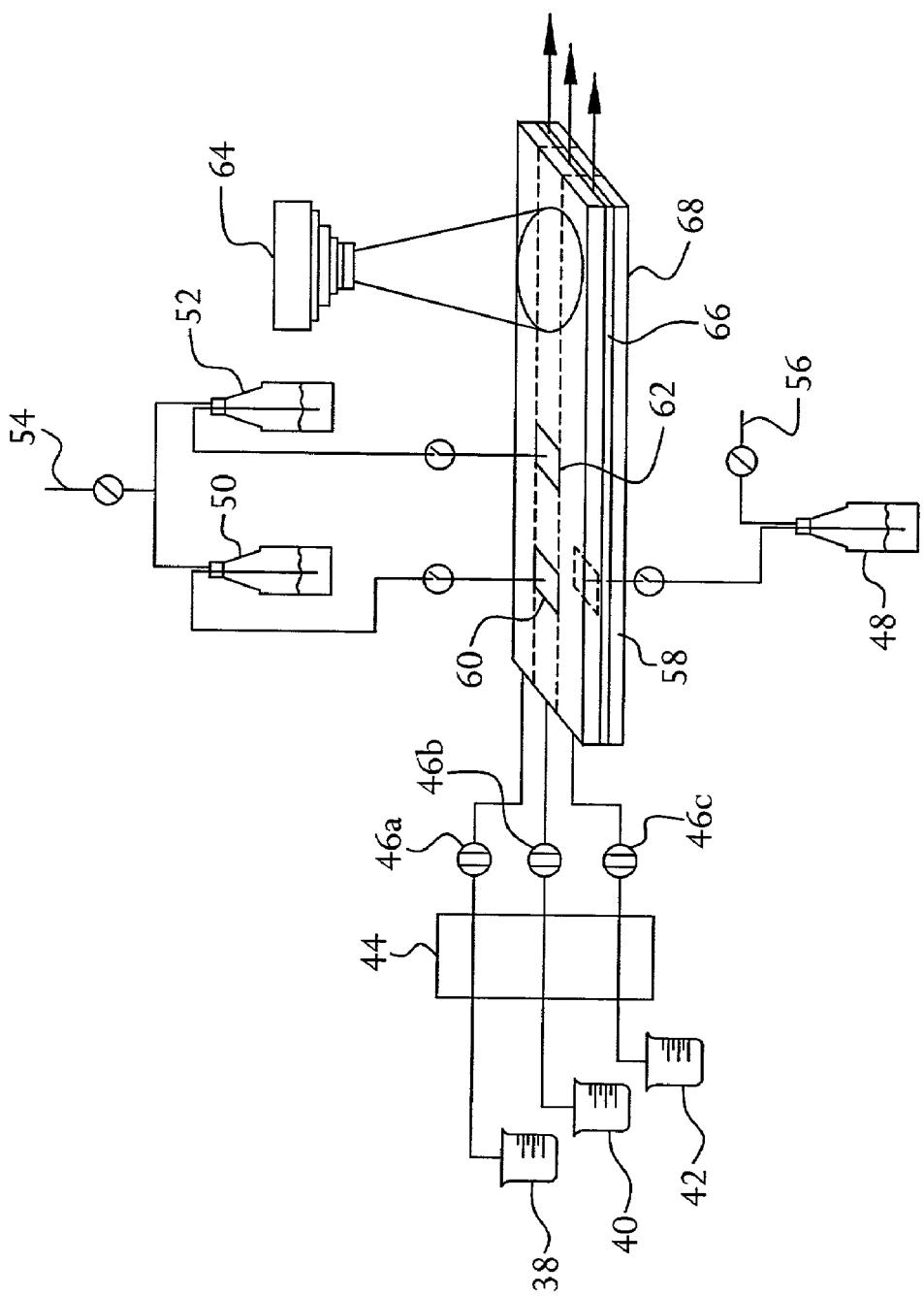
FIG. 3 schematically depicts an apparatus comprising a flow cell of the invention wherein the interactions of substances in the cell are directly viewed or imaged by a detector.

An apparatus comprising a flow cell of the present invention and a detector, is shown in FIG. 3. Samples 38, 40 and 42 are mechanically pumped by multichannel peristaltic pump 44 through valves 46a-c into a flow cell 68. The fluids may be driven by any appropriate means, such as by mechanical pumping with a single or multichannel peristaltic pump or a single or multichannel syringe pump, by gravity, by a pneumatic pressure source, by electrostatic force, or a combination of such driving means. At a first point downstream from the injection point in fluid cell 68, a reagent 50 is introduced orthogonal to the sample fluid flows via port 60 in the top wall of flow cell 68, driven by pneumatic pressure source 54. Reagent 48 is optionally added through port 58 in the cell bottom, driven by an independent pneumatic pressure source 56. At a later "downstream" point, a third reagent 52 is optionally added, driven by pneumatic pressure source 54 and enters the flow cell through port 62. A photodetector 64 is positioned to analyze the fluid flows downstream of the reagent introduction ports. Separate forces may optionally be used to drive the orthogonal fluid flows.

Figure 4:
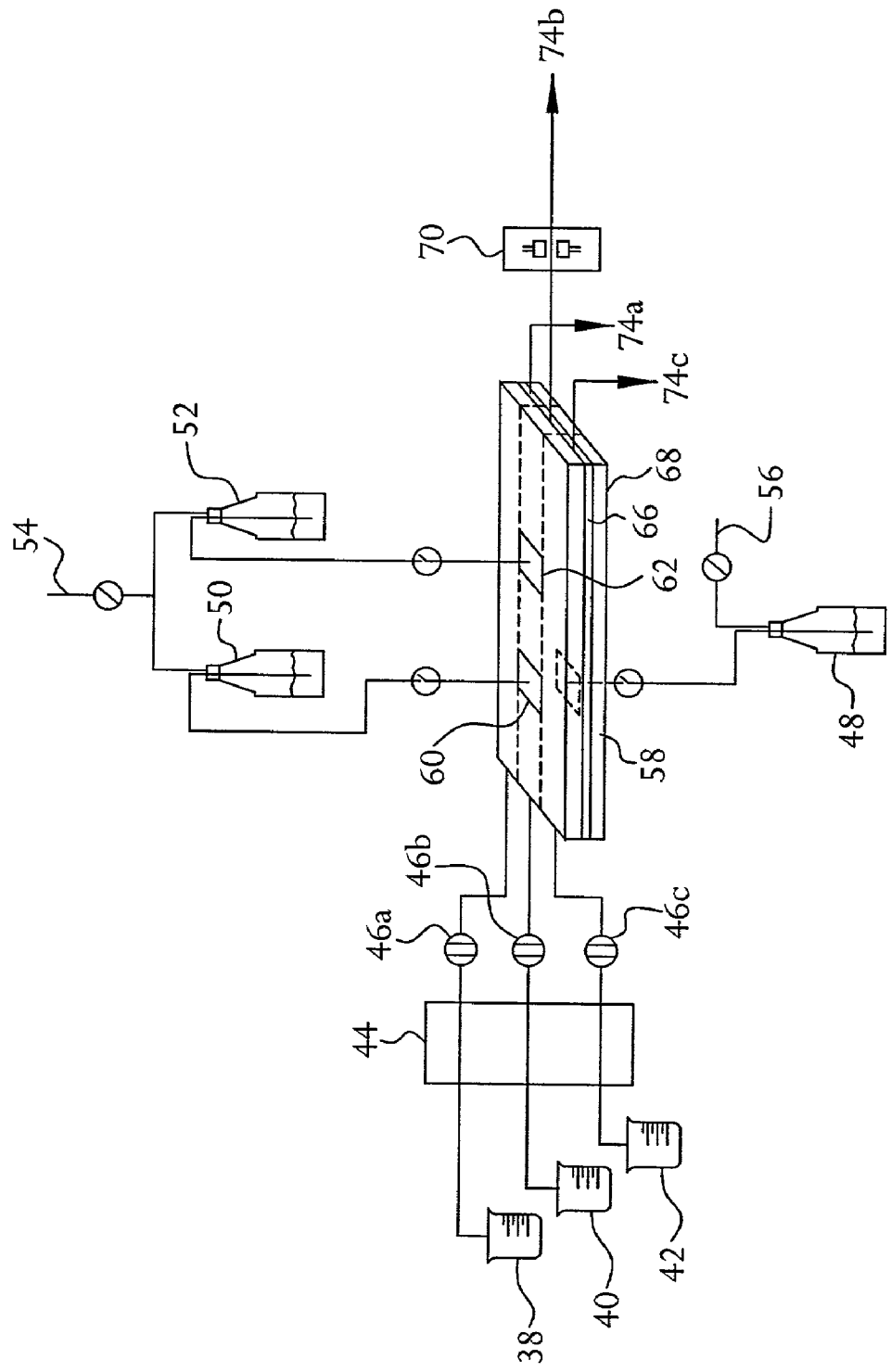
FIG. 4 schematically depicts an apparatus comprising a flow cell of the invention similar to FIG. 3, but where an effluent of the cell is analyzed by spectrophotometric analysis.

FIG. 4 illustrates an apparatus similar to the FIG. 3 apparatus, but containing a detector 70 in communication with the flow cell. Detector 70 is configured to analyze a selected fraction 74b of the flow cell effluent. Remaining fractions 74a and 74b flow to waste, to a recovery container or to an alternate detector configured in parallel with detector 70.

The analysis of the interaction between a reagent and a target substance according to the invention may employ any useful technique for analyzing chemical or biological samples. Such analytical techniques include, for example, spectrophotometry, infrared spectroscopy, fluorescence spectroscopy nuclear magnetic resonance and measurement of refractive indices. Interactions may also be analyzed by electrochemical techniques, or by qualitative wet chemistry techniques, wherein interaction of a target substance with a reagent produces a change which may be directly observed as by direct microscopic observation. In other embodiments, interactions may be analyzed by imaging and subsequent image analysis.

The spectrophotometer or other detector may be configured as in FIG. 3 to communicate optically with the chamber of the flow cell through a transparent wall. Alternatively, the detector may be positioned as shown in FIG. 4, in fluidic communication with fluid flow effluent from the cell or a selected fraction thereof. The detector may also be optically in communication with the chamber via a fiber optic connection.

Chemical reactions occurring in the flow cell as a result of interactions between reagents and target substances, or interactions between reagents in the interfacial zone between adjacent fluid flows, may be signaled by a visible color change, a fluorescence, a chemiluminescence or formation of an electrochemically active product. Color development, fluorescence or chemiluminescence can be followed by spectrophotometric detection through the top or bottom walls of the flow cell or through an optically transparent spacer. An electrode array may be integrated into the flow cell for carrying out electrochemical detection. Color development, fluorescence or luminescence emitting reactions can also be analyzed by providing an optical communication such as, for example through a fiber optic connection, between the flow cell and an appropriate detector. Measurements may be made before and/or after active mixing by a cross-stream or diffusion-based mixing of two or more fluid flows.

The product(s) of a chemical reaction may be analyzed visually or by a spectrophotometer. For example, a dilute ferric chloride solution interacting with a chemical compound having a phenol functionality produces a color change which qualitatively is consistent with a phenol. In addition, the interaction, as measured spectrophotometrically can be used to give more structural information than merely presence or absence of a phenol, or can be used to translate the amount of color produced by the interaction to a quantitative determination of the concentration of the phenol.

Since the extent of contact between a reagent and a target substance is controlled by the practice of the present invention, analysis of the interaction between the two materials can be performed before contact is made, after the interaction is complete, and at a point during the course of the interaction. For example, a solid target substance comprising cells or cells bound to beads may be analyzed by direct microscopic observation both before and after contact by one or more reagents.

Figure 5A:
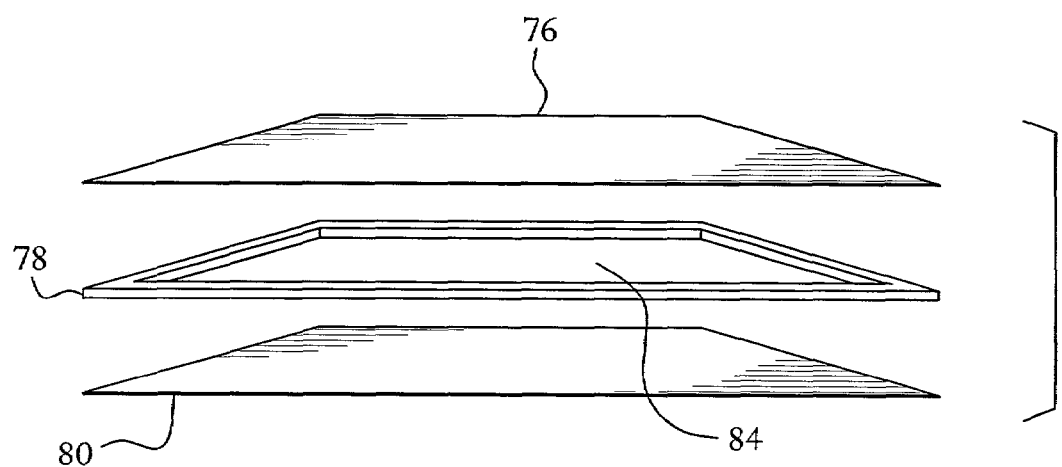
FIG. 5A represents an exploded view of the basic construction of a flow cell of the invention.
Figure 5B:
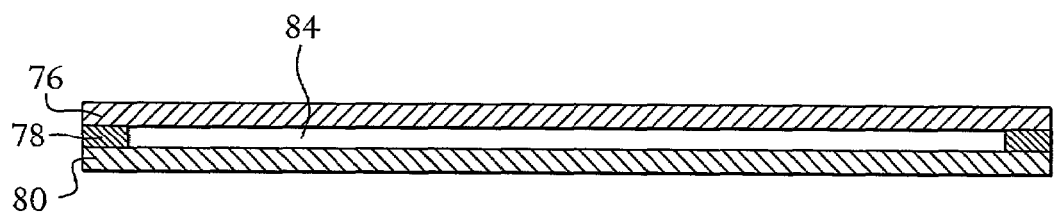
FIG. 5B depicts a cross sectional view of the construction of the flow cell of FIG. 5A.

The basic construction of a typical single chamber flow cell according to the present invention is shown in FIGS. 5A and 5B. The cell can be of any geometric shape, and is shown in FIG. 5A for purposes of illustration as a square. In other Figures other geometric shapes such as rectangular, triangular or polygonal are illustrated. The flow cell may comprise essentially any geometric shape. At least one chamber 84 which is typically substantially planar is formed between a top wall 76 and bottom wall 80. The walls are maintained in spaced relationship by a spacer, shown in FIG. 5A as gasket 78. The vertical distance between the top and bottom walls dictates the fluid flow depth. Maintaining the depth between the range of from about 50 to about 1000 microns prevents intermixing by adjacent fluid flows except by passive diffusion. The thickness of the spacer determines the flow depth in the embodiment of FIG. 5A.

Figure 6A:
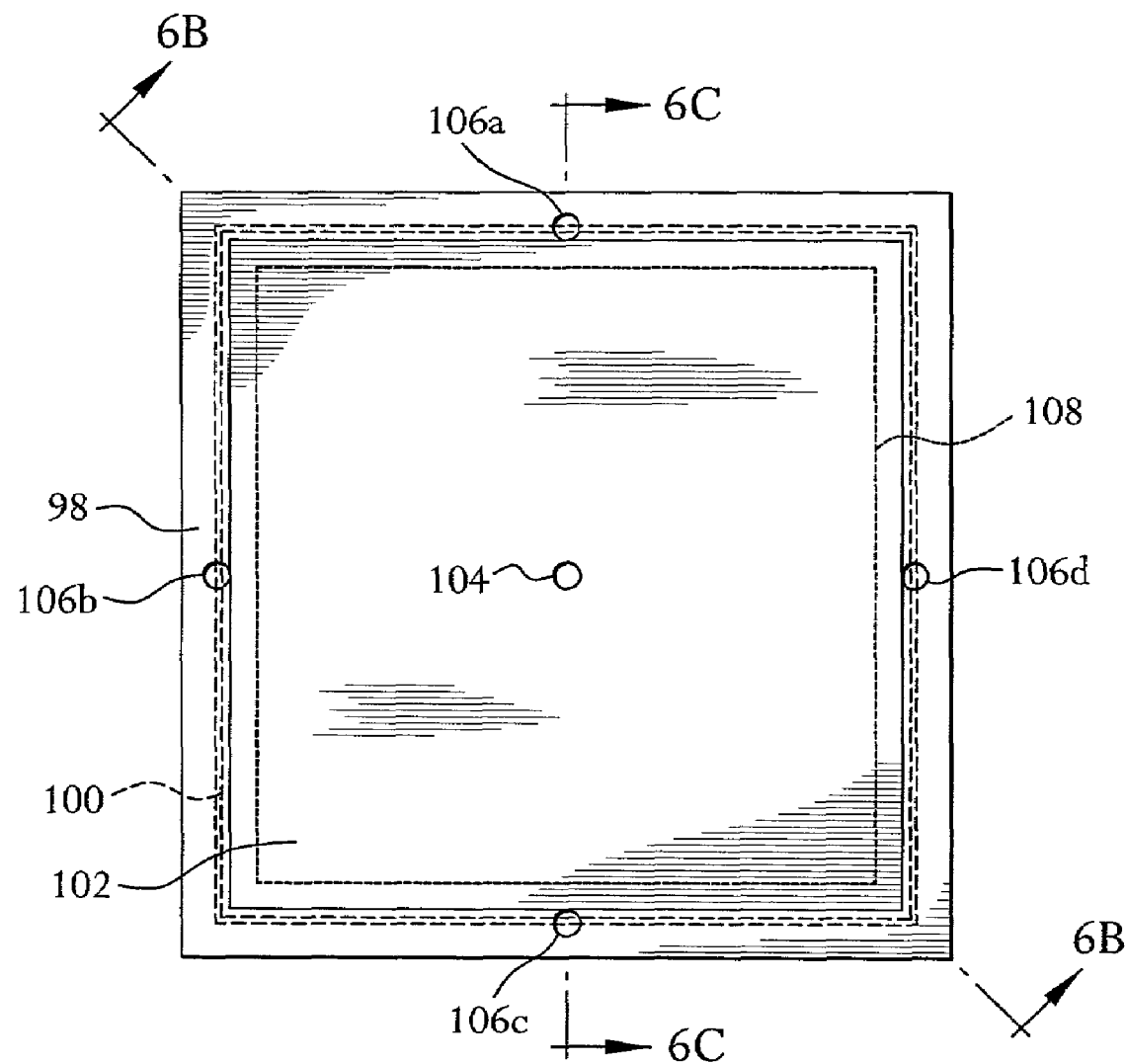
FIG. 6A is a top view of another flow cell embodiment of the invention containing a perimeter electrode.
Figure 6B:
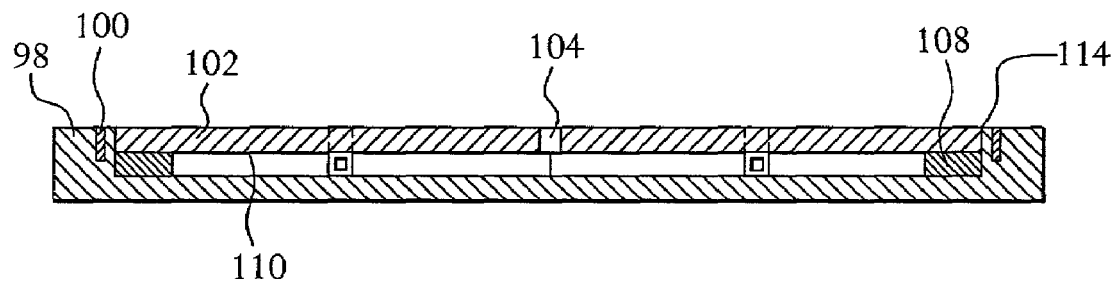
FIG. 6B is a cross-sectional view of the flow cell of FIG. 6A taken along line 6B-6B.
Figure 6C:
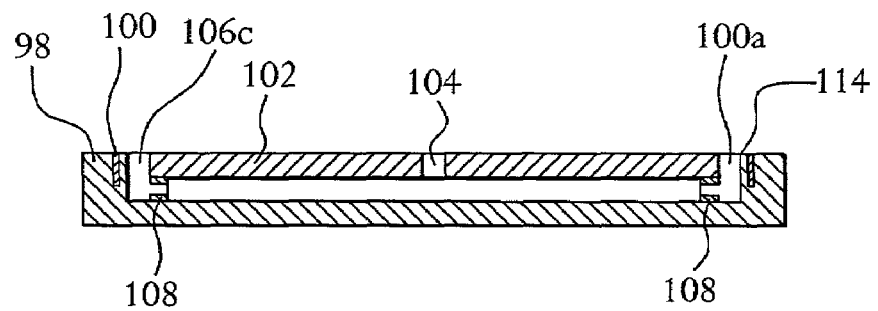
FIG. 6C is a cross-sectional view of the flow cell of FIG. 7A, taken along line 6C-6C.
Figure 7:
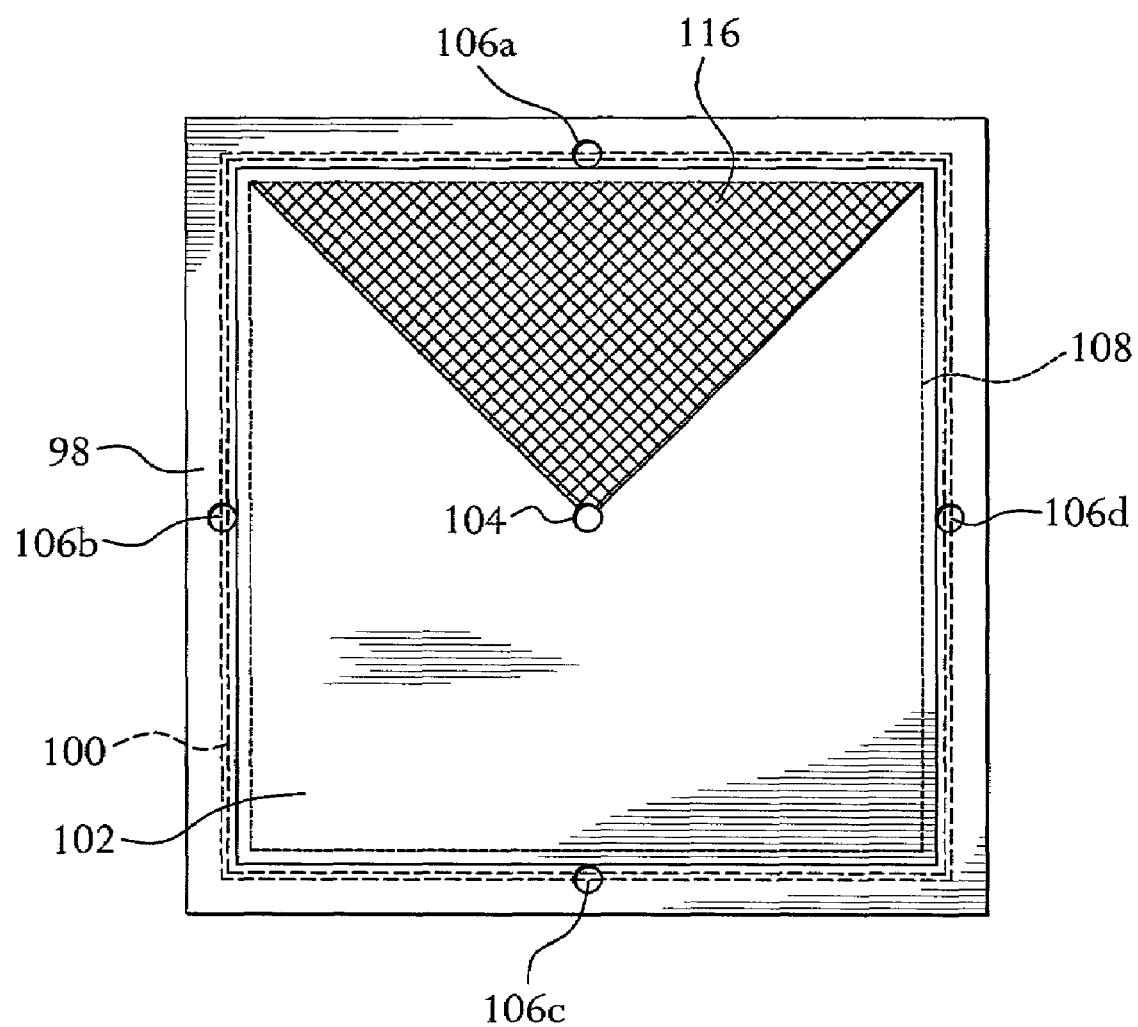
FIG. 7 is a top view of the flow cell of FIG. 7A illustrating an electrophoretically created fluid flow boundary.

FIGS. 6A-6C show another flow cell of the invention including an electrode in communication with a flow cell chamber. Top wall 102 and bottom wall 98 are separated by spacer 108 to create chamber 110. Bottom wall 98 has a machined recess 114 into which top wall 102 fits such that it is coplanar with bottom wall 98 and such that an outer perimeter portion of the bottom wall forms a support structure for the flow cell. Fluids enter the cell through inlets 106*a-d* through the spacer 108 located centrally at each edge of the top wall to establish four fluid flows. An electrode 100 around the perimeter of the flow cell is connected to the fluid inlets 106*a-d* and a single outlet 104 located centrally in the cell top wall. Outlet 104 also serves as the counter electrode. Appropriate gaps are machined into the support structure portion of bottom wall 98 and into spacer 108 at the center of each side, to accommodate fluid flow through inlets 106*a-d*. Individual isoconductive fluids that generate the same magnitude and direction of electroosmotic flow are introduced into the cell chamber via inlets 106*a-d*. High voltage is applied to the perimeter electrode 100. The counter electrode 104 is grounded. The resulting electrophoretically driven fluid flow pattern is depicted in FIG. 7, showing fluid boundary 116.

It may be appreciated that the single perimeter electrode 100 in FIG. 6A may be replaced by a plurality of independent electrodes which are not connected to one another. The same of different voltages may be applied to the electrodes. The voltage applied to the electrodes may be held constant or varied as a function of time.

Figure 8:
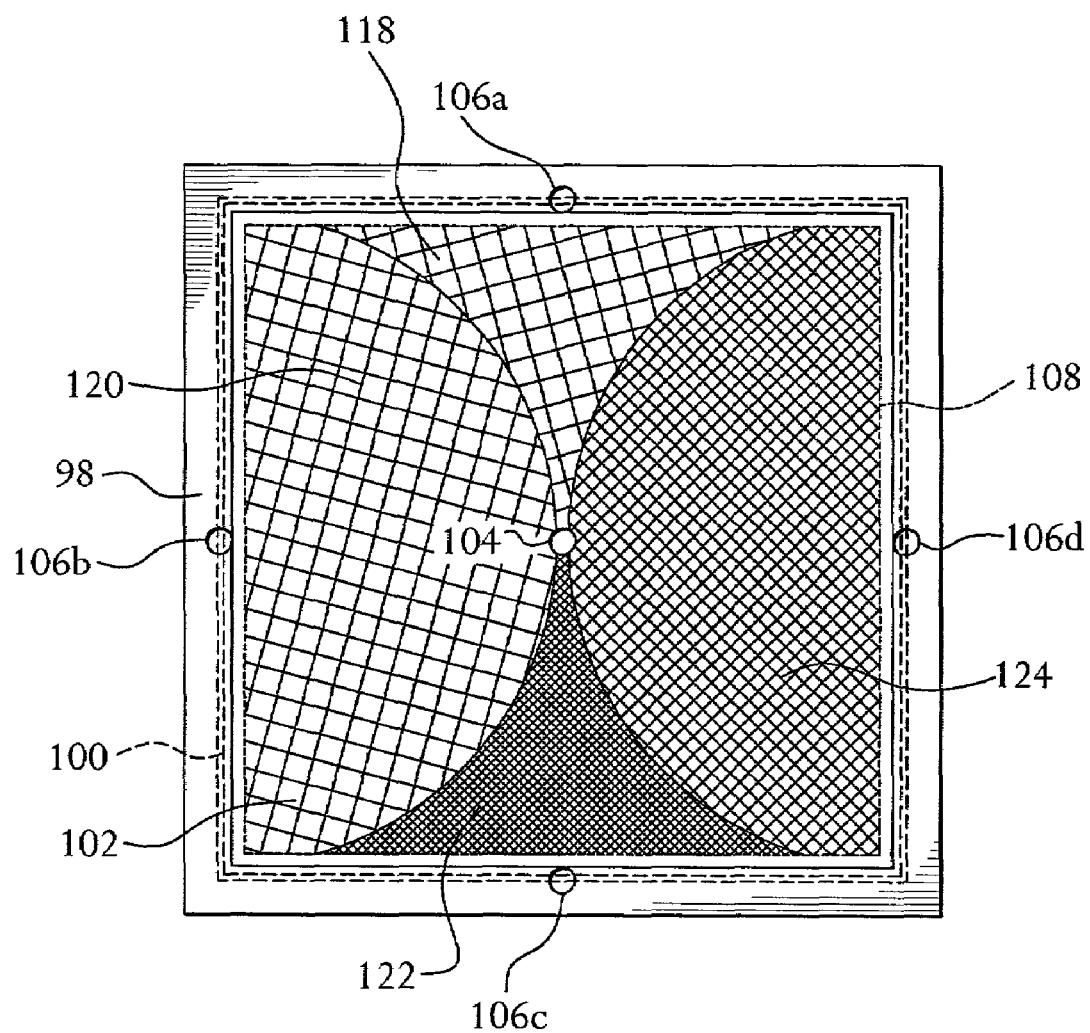
FIG. 8 is a top view of the flow cell of FIG. 7A illustrating electrophoretically driven fluid flow.

The flow cell of FIGS. 6A-6C may be operated under electroosmotic conditions when reagents contained in the fluid flow comprise charged compounds. A representative flow pattern is shown in FIG. 8 which occurs when the electroosmotic flow of fluids 120 and 124 is higher than those of fluids 118 and 122.

Figure 9:
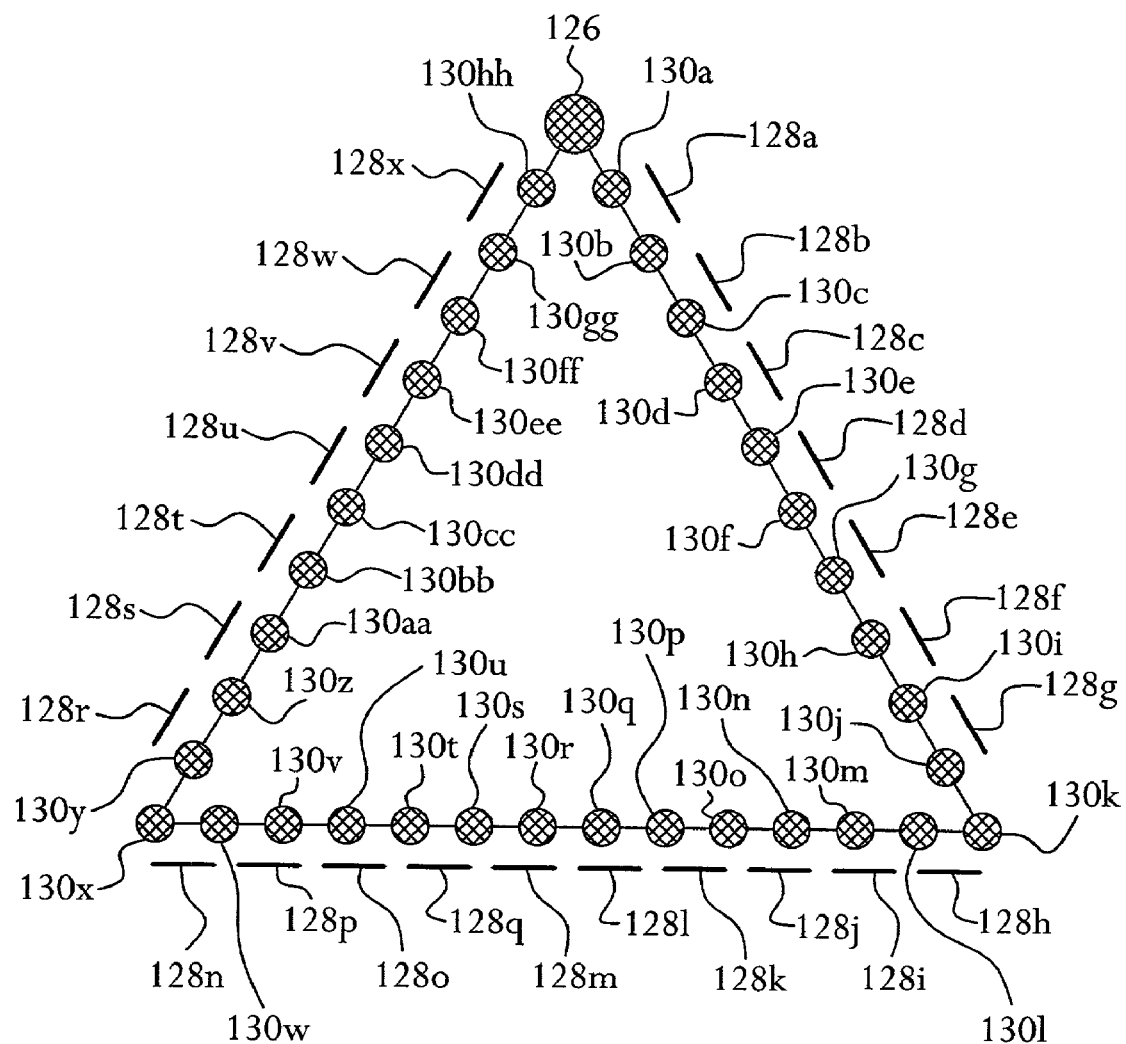
FIG. 9 is a schematic representation of a flow cell of the present invention having a series of ports and a series of independent electrodes at the perimeter of the cell.

Another embodiment of the flow cell of the present invention is schematically represented by FIG. 9. The cell contains a grounded inlet 126, discrete perimeter electrodes 128*a-x* and perimeter ports 130*a-hh* which may be employed as inlets or outlets. This flow cell may be configured for varied applications, including, but not limited to the applications depicted in FIGS. 10 and 11.

Figure 10:
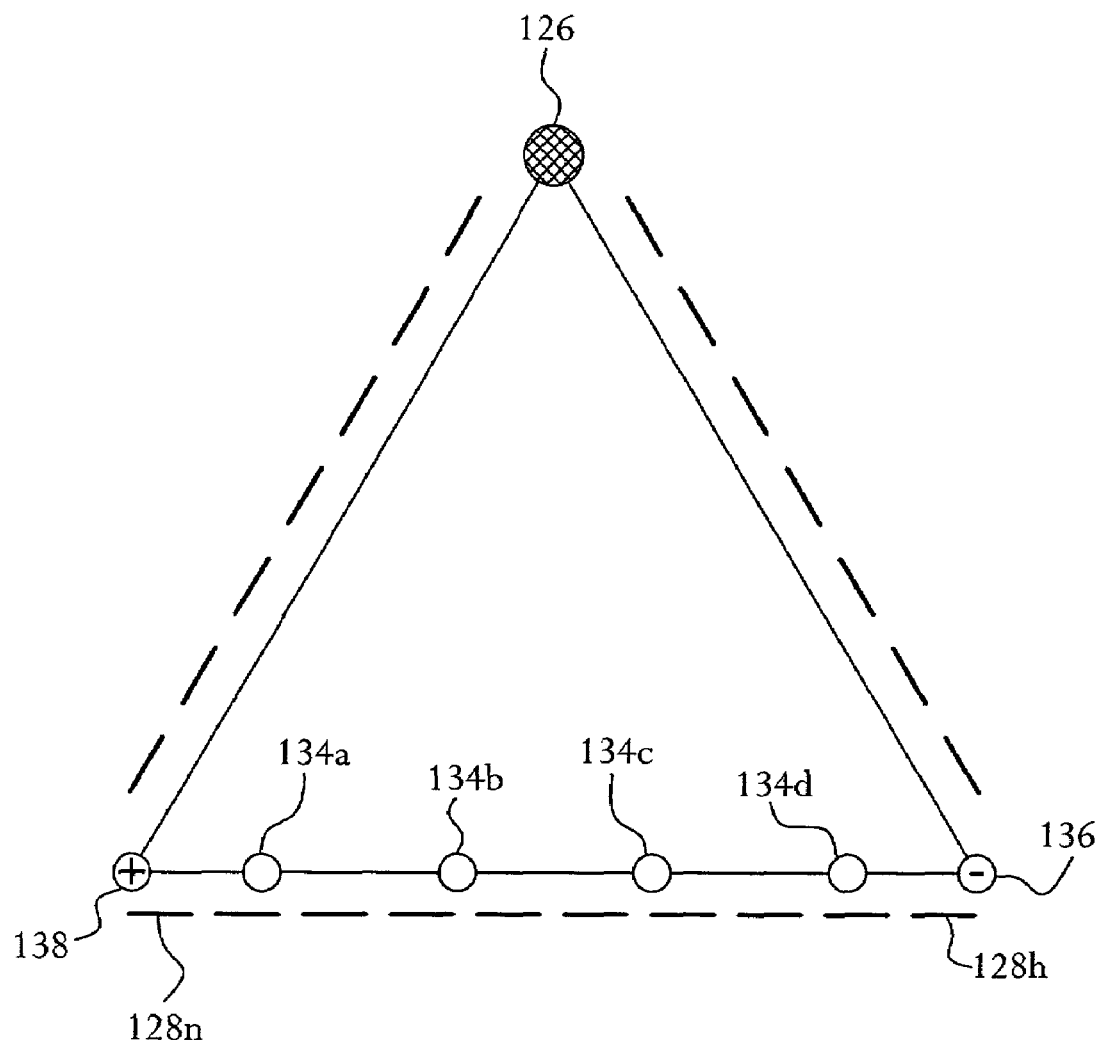
FIG. 10 is a schematic representation of a flow cell of the invention having a grounded fluid inlet, a positively charged fluid outlet and a negatively charged fluid outlet.
Figure 11:
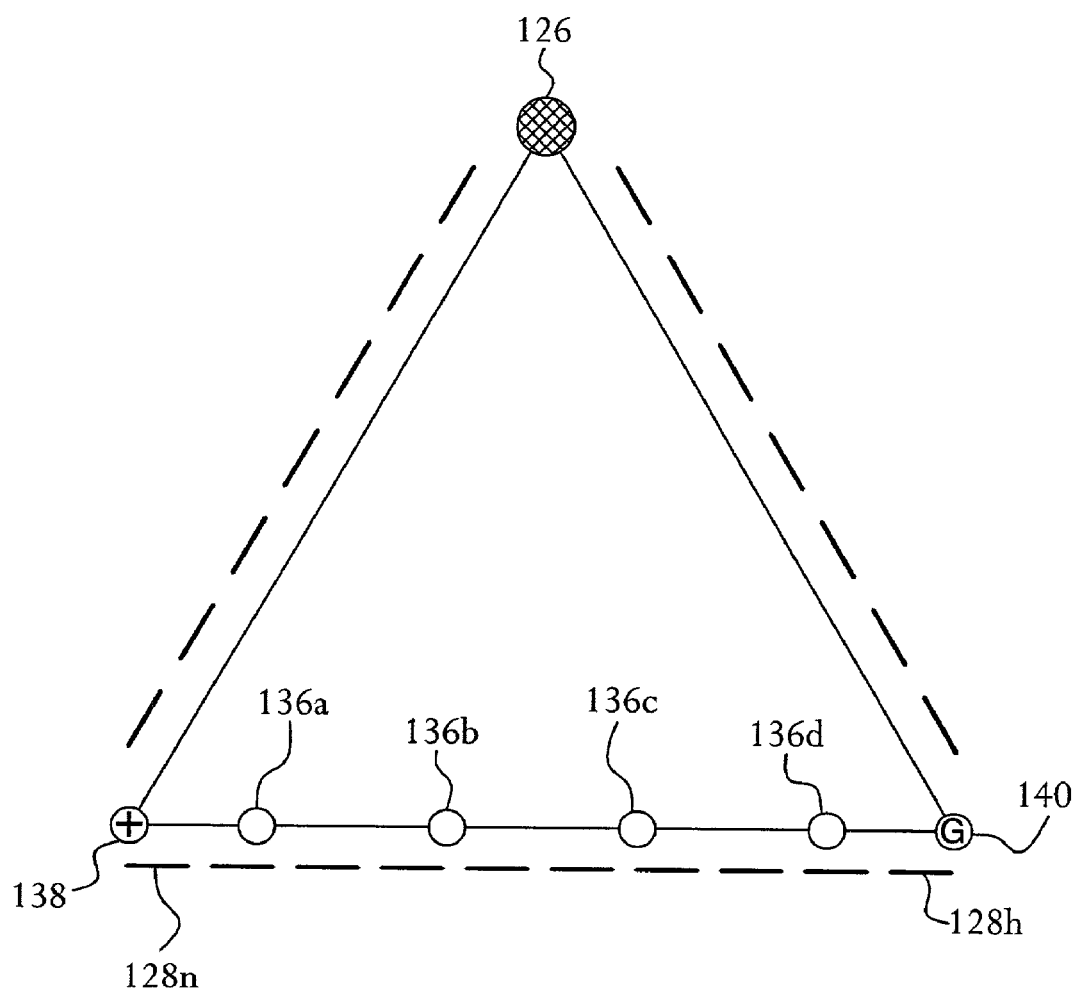
FIG. 11 is a schematic representation of a flow cell of the invention having a grounded fluid inlet, a positively charged fluid outlet and a grounded fluid outlet.

FIG. 10 schematically depicts a variation of the FIG. 10 flow cell containing a single grounded fluid inlet 126, a single positively charged fluid outlet 138, and a single negatively charged fluid outlet 136. A plurality of electrically floating fluid outlets 134*a-d* are positioned on the perimeter of the cell top wall between the positive and negative outlets. Fluid outlet 138 is connected to a+1 kV electrode 128*n* and fluid outlet 136 is connected to a−1 kV electrode 128*h*. A fluid containing a mixture of at least one positively charged species and at least one negatively charged species enters the cell through fluid inlet 126 and exit through a series of fluid outlets including 136, 138 and 134*a-d*. The flow cell of FIG. 11 can be used for the continuous free solution electrophoretic preparative isolation of one or more components. In one embodiment, a dilute solution containing both a positively charged organic compound and a negatively charged organic compound is introduced into a flow cell as depicted in FIG. 11, through inlet 126. The negatively charged compound is isolated in pure form from the positively charged outlet 138 and the positively charged compound is isolated in pure form from the negatively charged outlet 136.

FIG. 11 schematically depicts another variation of the FIG. 10 flow cell containing a single grounded fluid inlet 126, a single positively charged fluid outlet 138, and a single electrically grounded fluid outlet 136. A plurality of electrically floating fluid outlets 136*a-d* are positioned on the perimeter of the cell top wall between the positive outlet 138 and the grounded outlet 140. Fluid outlet 138 is connected to a+1 kV electrode 128*n*. A fluid containing a mixture comprising at least one charged species enters the cell through fluid inlet 126 and exit through a series of fluid outlets including 140, 138 and 134*a-d*. The flow cell of FIG. 12 can be used for the continuous free solution electrophoretic preparative isolation of one or more components. In one embodiment, a solution of two ionic species of the same charge is introduced through fluid inlet 126. The ion of highest mobility moves faster towards the positive electrode 138, relative to the other species. Thus the proportion of higher mobility species to lower mobility species in the eluent collected from the outlet ports increases in the order 140<136*d*<136*c*<136*b*<136*a*<138.

Figure 12A:
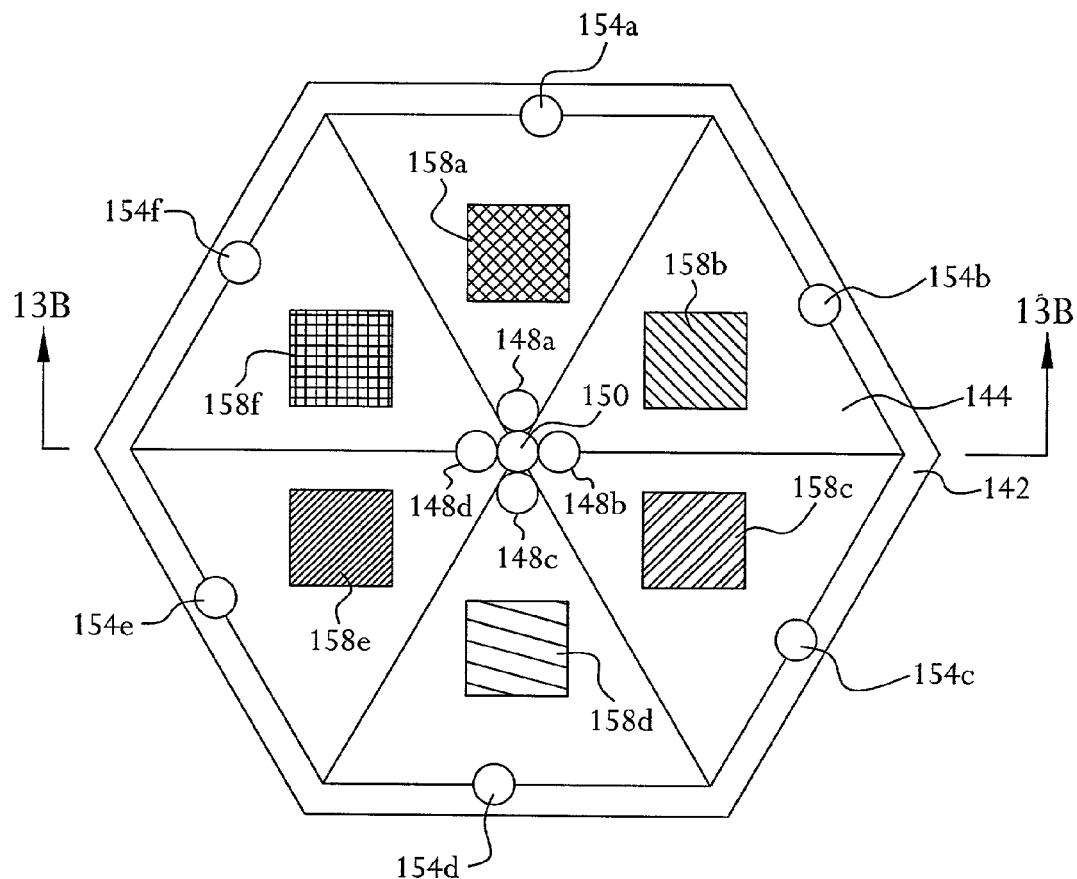
FIG. 12A is a top view of a flow cell of the invention having a plurality of inlets and outlets and a plurality of immobilized solid target substances.
Figure 12B:
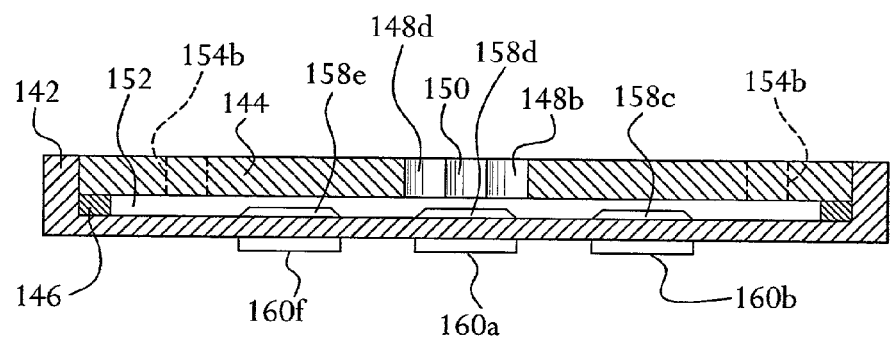
FIG. 12B is a cross-sectional view of the flow cell of FIG. 12A taken along line 12B-12B.

Flow cells of the present invention may be configured to accommodate multiple solid target substances such as beads, cells and cell fragments. FIGS. 12A-B show a polygonal flow cell having a six-zone chamber 152 bounded by top wall 144, bottom wall 142 and spacer 146. An accumulation of beads or cells 158*a-f* is contained in each chamber segment, each segment containing a different bead type. Where ferromagnetic beads are employed, they may be held in place in the chamber by an area of a metal oxide formed into the cell top or bottom wall, or by placing magnets 160*a-f* beneath the cell bottom wall. The beads or cells may be held in place with or without an applied electric field or magnetic field. A plurality of fluid reservoirs 148*a*-148*d* atop the cell top wall communicate with a common inlet 150 to provide reagent-containing fluids or wash media. Once the beads or cells are placed in the chamber, they are perfused with fluids either individually or in combination via the common inlet 150. Fluid flow may be driven either by electroosmosis, by mechanically pumping or may be pneumatically pressurized flow. Valve-controlled outlets 154*a-f* are provided at the periphery of the cell for removing fluids. Observations of the fluid/bead interactions may be made continuously or at any desired time. At the end of the experiment, the beads or other solid material comprising the target substance are flushed out by a high flow liquid. Flushing may also be performed by applying an alternating current (AC) field between the top and bottom walls of the cell between conductive transparent coatings on the cell top and bottom walls. Such coatings may comprise indium tin oxide, for example coating.

The flow cell of FIGS. 12A-B may be conveniently employed to analyze a cell population's interaction with various drugs. Accordingly, the same cell type is introduced into the six cell segments. Different drugs are introduced in fluids from reservoirs 148a-148d, which are flowed to the cell accumulations in the respective zones. Alternatively, a single drug's interaction between different populations of cells may be analyzed by depositing cells in the chamber segments and contacting the cells in each segment with the same drug.

The apparatus of FIGS. 12A-B may be utilized in a cell immunofluorescence assay, to determine the presence of a selected antigen on the surface of a given cell type. Cells, comprising either the same or different cell populations, are placed in the chambers of the flow cell. Fluid containing a fluorescence-labeled antibody which binds the selected antigen in flowed though the cell. Methods for labeling antibodies with fluorescent labels are well-known to those skilled in the art. Excess fluorescence is washed away and the fluorescence signal is observed, e.g., by fluorescence microscopy, emitting from cell populations bearing the fluorescent tag, and thus the selected antigen. A fluorescence image may be made with a charge-coupled device and stored electronically or stored chemically such as in a photograph and the image analyzed at a different time. It may be appreciated that the same procedure may be adapted to identify the presence of a desired antibody on a population of cells, by probing with an appropriate labeled antigen.

FIGS. 13A-13B depict the flow of adjacent fluids in a flow cell according to the invention wherein adjacent fluid flows are allowed to mix in a controlled manner by varying the fluid flow rate, and thus the degree of intermixing of the fluids. Reducing the flow rate provides increased intermixing. Reducing the flow rate also increases the residence time of the fluids in the flow cell. The residence time may also be increased by increasing the flow path. FIG. 13A is a schematic representation of the mixing of the following fluids at steady state, comprising 0.5M solutions of the following reactants flowing at 0.07 mL/min: $K_3Fe(CN)_6$, 190a; $FeCl_3$; 190b and KSCN 190c. Regions 198a and 200a represent, respectively the development of the reaction products $Fe(SCN)^{63-}$ and $Fe[Fe(CN)_6]$, as the flowing reactant streams diffuse into each other. Broader reactant zones are observed in FIG. 13B, where the reactant flow rate was reduced to 0.008 mL/min. In FIG. 13C the flow cell further comprises a pair of ports, 204a and 204b, which provide a cross-wise fluid flow preferably in a pulsatile flow, which achieves active mixing of fluids 202a, 202b and 202c. This fluid flow is orthogonal to the plurality of reagent-containing flows and in the same common plane. In FIG. 13C, flows 202a-c interact slowly by the process of passive diffusion until they reach the point where they are contacted by transverse flows 204a and 204b. At this point, active mixing of flows 202a-c occurs.

Figure 14A:
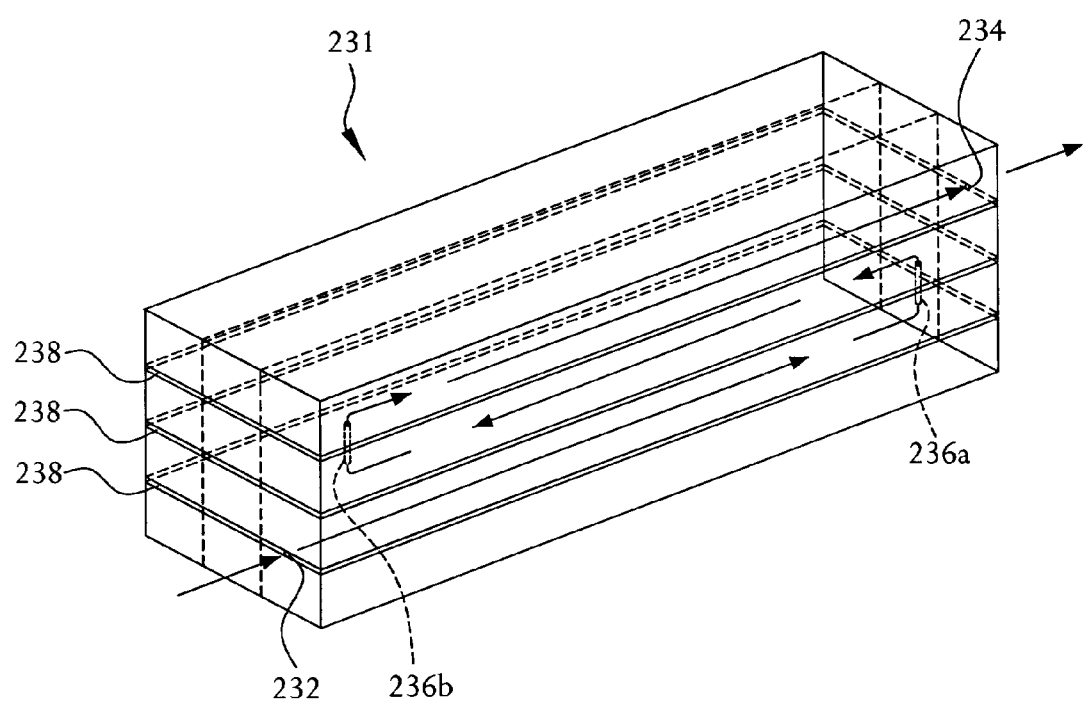
FIG. 14A is a perspective view of a multi-layered flow cell according to the present invention.
Figure 14B:
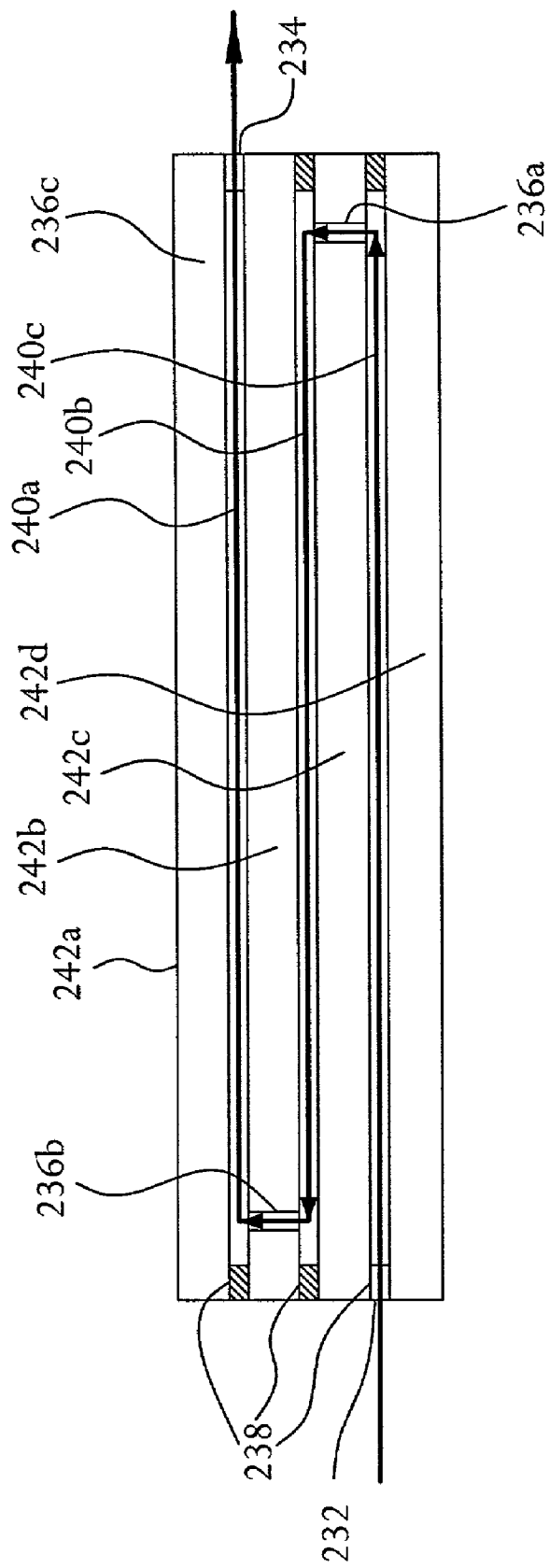
FIG. 14B is a detailed side-view of the flow cell of FIG. 14A.

The flow cells of the present invention may be arranged in a stacked array, generally designated as 231 in FIG. 14A. The flow cell has four walls 242a-d, separated by spacers 238 to form three chambers 240a-c. The fluid flow traverses these chambers through connections provided between adjacent chambers. It may be appreciated that the flow path is thus increased by a factor of three in the three-level cell of FIG. 14A. As shown in FIG. 14B, fluid enters the bottom chamber 240c through inlet 232, traverses the length of the cell, enters second chamber 240b through inlet 237a, traverses the length of the cell again, enters the third chamber 240a through inlet 236b, traverses the length of the cell and exits the cell through outlet 234.

A major advantage of capillary electrophoresis is low sample requirements. But detection of analyte becomes more difficult as the sample size is made smaller. Optical absorbance based detection is therefore rarely useful in microchip-based capillary electrophoresis. The flow cell of the present invention is microscale in the depth dimension only, and macroscale in the length and width dimensions. Absorbance detection of analytes is possible in flow cells of the present invention. The fluid channel width may be used as the path length for measuring optical absorbance, even in flow cell having a width of as little as 1 millimeter.

Figure 15:
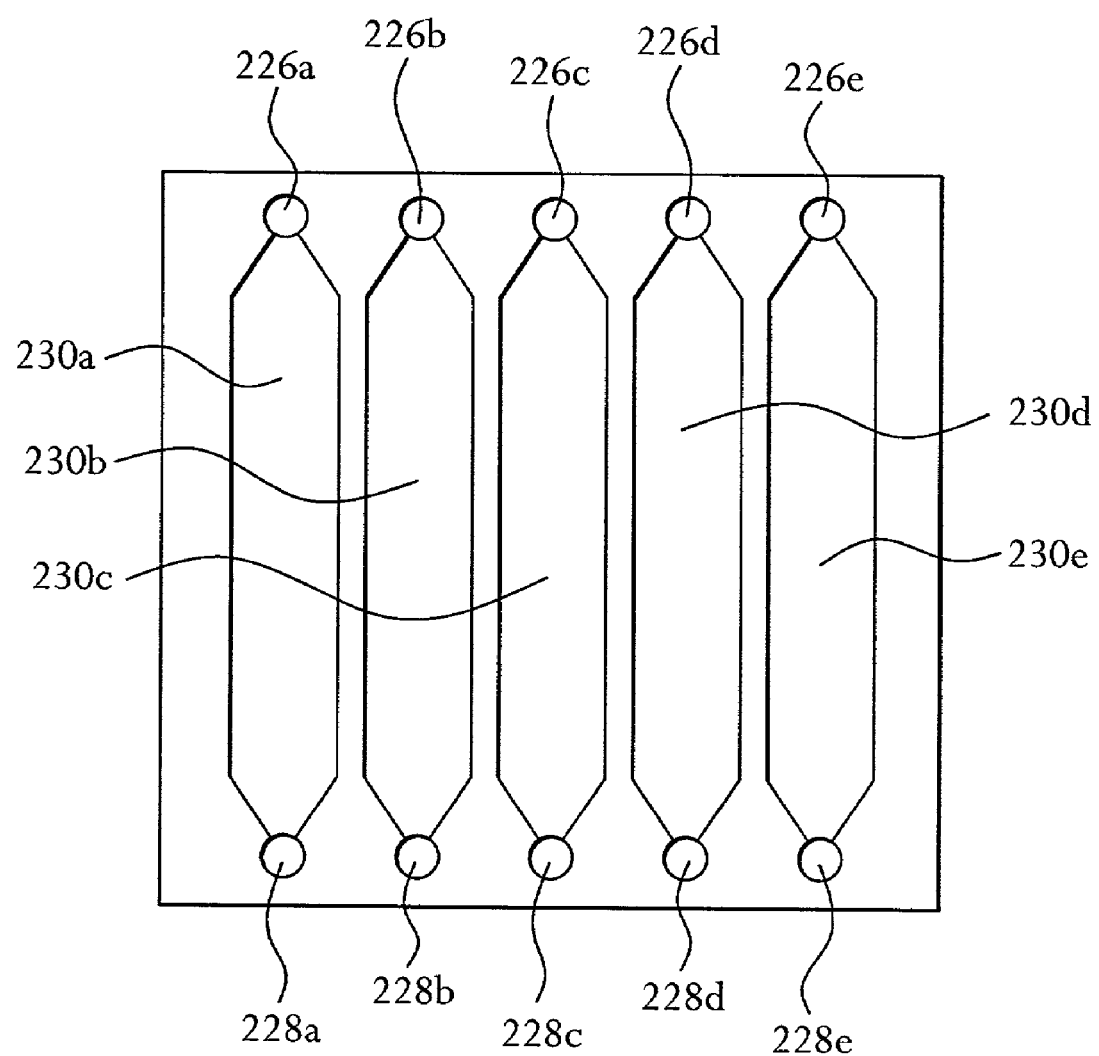
FIG. 15 is a top view of a multiple channel flow cell according to the present invention.

Flow cells of the present invention may be constructed in parallel arrays such as shown in FIG. 15. Multiple fluidically isolated channels 230a-e are die cut into the cell spacer. Sample inlet ports 228a-e are provided at one end of each parallel channel and corresponding sample outlet ports 226a-e are provided at the other end.

All references cited herein are incorporated by reference. The present invention may be embodied in other specific forms without departing from the spirit or essential attributes thereof and, accordingly, reference should be made to the appended claims, rather than to the foregoing specification, as indication of the scope of the invention.

What is claimed is:

1. A method for analyzing interactions between reagents and target substances, comprising:
   (a) providing at least three primary fluid flows in substantially the same plane, said primary fluid flows all being adjacent simultaneous substantially parallel fluid flows, wherein said primary fluid flows are contained in a chamber having at least one internal cross-sectional dimension of less than 1000 microns, and wherein at least one of said primary fluid flows comprises a target substance and is flanked on each side by a primary fluid flow, and wherein the primary fluid flows flanking said target-comprising primary fluid flow comprise, respectively, a first reagent and a second reagent capable of reacting with the target substance;
   (b) providing one or more secondary fluid flows, said secondary fluid flow(s) located in a plane that is substantially orthogonal to the plane of said primary fluid flows, wherein each of said secondary fluid flows is introduced into one of said primary fluid flows comprising a target substance, and wherein at least one secondary fluid flow comprises a third reagent capable of reacting with the target substance; and
   (c) monitoring reactions between reagents and target substances.

2. The method of claim 1, wherein at least one primary fluid flow comprising a target substance is contacted with one or more of said primary fluid flows comprising a reagent (a) prior to providing said one or more secondary fluid flows, (b) after providing said one or more secondary fluid flows, or (c) before and after providing said one or more secondary fluid flows.

3. The method of claim 1, wherein the target substance is selected from the group consisting of cells; isolated cell fractions; beads displaying on their surfaces chemical functional groups, biological molecules, or cells; and combinations thereof.

4. The method of claim 1 wherein the target substance is monitored before and after contact with the first reagent, the second reagent or the third reagent.

5. The method of claim 1 wherein said primary fluid flow comprising a target substance is contacted with said first and second reagents, said primary fluid flows having flow rates tuned to provide contact between said target substance and said first and second reagents in a flow zone containing only target substance and said first reagent, a flow zone containing only said target substance and said second reagent, and a flow zone containing said target substance and said first and second reagents wherein interactions at each of the flow zones are monitored.

6. The method of claim 1, wherein a cell culture comprising motile cells is contacted with two or more of said primary fluid flows and analysis is performed on movement of said motile cells between said fluid flows.

7. The method of claim 1, wherein flow rates of one or more of any of the fluid flows are varied so as to vary at least one of (i) the reaction time of the reagent with the target substance or (ii) the amount of diffusion-based intermixing occurring between adjacent fluid flows.

8. The method of claim 1 wherein two or more of said primary fluid flows contain different reagents and contact the same target substance.

9. The method of claim 1 wherein said secondary fluid flows are either constant or pulsatile, such that pulsatile fluid flows result in mechanical intermixing of said secondary fluid flows and said primary fluid flows.

10. The method of claim 1 wherein interactions are monitored through spectrophotometry, electrochemistry or microscopy.

11. The method of claim 1 wherein one or more of said fluid flows are driven by mechanical pumping, gravity, pneumatic pressure, electrostatic force, or a combination thereof.

12. The method of claim 1 wherein the target substance(s) are chosen from the group consisting of peptides, polypeptides, antigens, antibodies, oligonucleotides, polynucleotides, carbohydrates and polysaccharides.

13. The method of claim 1 wherein the spatial relationship of the fluid flows is determined by a pattern of inlets and outlets from the chamber.

14. The method of claim 13 wherein, relative to the fluid flow direction, the inlets are offset from the outlets.

15. The method of claim 13 wherein the inlets are located at substantially the center of the chamber and the primary fluid flows radially outward from the center.

16. The method of claim 1 wherein the spatial relationship of the fluid flows is determined by the relative velocities of the fluid flows.

17. The method of claim 1 wherein the spatial relationship of the fluid flows is determined by electrodes which attract electrolytes in the fluids.

18. The method of claim 1 wherein all of said secondary fluid flows comprise different reagents.

19. The method of claim 1 wherein said one or more secondary fluid flows are introduced into the chamber at its smallest dimension.

20. A method for analyzing interactions between reagents and target substances, comprising:
(a) providing three or more adjacent simultaneous substantially parallel fluid flows in substantially the same plane, wherein said three or more adjacent simultaneous fluid flows are contained in a chamber having at least one internal cross-sectional dimension of less than 1000 microns, at least one of said fluid flows comprising a reagent capable of reacting with a target substance and at least one other of said fluid flows comprising a target substance;
(b) adjusting one or more of flow rate, length of the flow path, and internal cross-sectional dimension to thereby control the desired quantity and rate of intermixing by passive diffusion such that said intermixing by passive diffusion creates three flow zones in any middle flow that is between two other adjacent simultaneous flanking fluid flows, a first flow zone containing the middle fluid flow and only one of said flanking fluid flows, a second flow zone containing the middle fluid flow and only the other of said flanking fluid flows, and third flow zone containing the middle fluid flow and both of said flanking fluid flows; and
(c) monitoring reactions between reagents and target substances at each of the flow zones.

21. A method for analyzing interactions between reagents and target substances, comprising:
(a) providing two or more primary fluid flows in substantially the same plane, said primary fluid flows being adjacent simultaneous substantially parallel fluid flows, wherein said two or more primary fluid flows are contained in a chamber having at least one internal cross-sectional dimension of less than 1000 microns, said chamber having a pair of ports that are capable of providing a secondary fluid flow in a direction nonparallel to that of said adjacent simultaneous fluid flows to thereby induce intermixing of said primary fluid flows, said ports being located on substantially opposite sides of said chamber, and wherein at least one of said primary fluid flows comprises a reagent capable of reacting with a target substance and at least one other of said primary fluid flows comprises the target substance;
(b) contacting with a target substance one or more of said primary fluid flows comprising a reagent; and
(c) monitoring reactions between reagents and target substances.

22. A method for analyzing interactions between reagents and target substances comprising:
(a) providing two or more adjacent simultaneous fluid flows in substantially a single plane wherein said two or more adjacent simultaneous fluid flows are contained in a chamber having at least one internal cross-sectional dimension of less than 1000 microns, said chamber having at least one electrically grounded fluid inlet and a plurality of ports located substantially at the perimeter of the chamber, wherein said ports independently function as either fluid inlets or fluid outlets, wherein there is one fluid inlet for each of said adjacent simultaneous fluid flows and at least one fluid outlet, said chamber additionally having one or more electrodes around its perimeter such that the applying voltage to said electrodes will result in electrophoretically driven fluid flow, and wherein at least one of said fluid flows comprises a reagent;
(b) contacting one or more of said adjacent simultaneous fluid flows with a target substance; and
(c) monitoring reactions between reagents and target substances.

23. The method of claim 22 wherein said secondary fluid flow is a pulsating fluid flow.

24. The method of claim 22 wherein said inlets and outlets are substantially orthogonal to the substantially single same plane of said adjacent simultaneous fluid flows of step (a).

25. The method of claim 22 wherein said chamber additionally has one or more ports located substantially at the center of the chamber and extending substantially orthogonally to the internal cross-sectional dimension of less than 1000 microns and wherein a single electrode is connected around the perimeter of the chamber and to said ports, said fluid outlets having counter electrodes along the edges thereof.

26. The method or claim 22 wherein a plurality of independent electrodes not connected to one another are placed around the perimeter of the chamber.

27. The method of claim 26 wherein a different voltage is applied to different electrodes.

28. The method of claim 22 wherein one port is a grounded fluid inlet, one port is a positively charged fluid outlet, and one port is a negatively charged fluid outlet.

29. The method of claim 28 wherein at least one fluid flow comprises a mixture of at least one positively charged species and one negatively charged species.

* * * * *